(12) United States Patent
Begtrup et al.

(10) Patent No.: US 10,405,794 B2
(45) Date of Patent: Sep. 10, 2019

(54) SWEAT CONDUCTIVITY, VOLUMETRIC SWEAT RATE, AND GALVANIC SKIN RESPONSE DEVICES AND APPLICATIONS

(71) Applicant: Eccrine Systems, Inc., Cincinnati, OH (US)

(72) Inventors: Gavi Begtrup, Cincinnati, OH (US); Jacob A. Bertrand, Norwood, OH (US); Jason Heikenfeld, Cincinnati, OH (US); Austin Morgan, Cincinnati, OH (US); Nathan Weinle, Cincinnati, OH (US)

(73) Assignee: Eccrine Systems, Inc., Cincinnati, OH (US)

( * ) Notice: Subject to any disclaimer, the term of this patent is extended or adjusted under 35 U.S.C. 154(b) by 0 days.

(21) Appl. No.: 15/653,494

(22) Filed: Jul. 18, 2017

(65) Prior Publication Data

US 2018/0020966 A1 Jan. 25, 2018

Related U.S. Application Data

(60) Provisional application No. 62/364,034, filed on Jul. 19, 2016, provisional application No. 62/464,610, (Continued)

(51) Int. Cl.
*A61B 5/00* (2006.01)
*A61B 5/01* (2006.01)
(Continued)

(52) U.S. Cl.
CPC .............. *A61B 5/4266* (2013.01); *A61B 5/01* (2013.01); *A61B 5/0533* (2013.01);
(Continued)

(58) Field of Classification Search
CPC ...................... A61B 5/14507–5/14521; A61B 5/4261–5/4266; A61B 10/0064
(Continued)

(56) References Cited

U.S. PATENT DOCUMENTS

| 4,190,060 A | 2/1980 | Greenleaf et al. |
| 4,383,529 A | 5/1983 | Webster |

(Continued)

FOREIGN PATENT DOCUMENTS

| EP | 0282349 A2 | 9/1988 |
| EP | 0453283 A1 | 10/1991 |

(Continued)

OTHER PUBLICATIONS

Nguyen, N. T. "Micromachined flow sensors—a review." Flow measurement and Instrumentation 8.1 (1997): 7-16. doi: 10.1016/S0955-5986(97)00019-8.*

(Continued)

*Primary Examiner* — Gary Jackson
*Assistant Examiner* — Jonathan Kuo
(74) *Attorney, Agent, or Firm* — Chad G. Clark

(57) ABSTRACT

The disclosed invention includes sweat sensing devices configured to periodically measure sweat conductivity and galvanic skin response, devices to measure volumetric sweat flow rate, and devices that combine the three functions. The disclosure further includes methods for using a device configured to perform periodic sweat conductivity measurements, galvanic skin response measurements, and volumetric sweat rate measurements so that each sensor modality informs composite estimates of sweat onset, sweat cessation, sweat ion concentration, and sweat rate. The method uses those measurements to inform other sweat sensing device functions, such as determining the existence of a physiologi- (Continued)

cal condition, or performing measurements of concentrations, ratios, and trends of sweat analytes.

8 Claims, 19 Drawing Sheets

Related U.S. Application Data filed on Feb. 28, 2017, provisional application No. 62/510,491, filed on May 24, 2017.

(51) Int. Cl.
    *A61B 5/053*     (2006.01)
    *A61B 5/145*     (2006.01)

(52) U.S. Cl.
    CPC ...... *A61B 5/14517* (2013.01); *A61B 5/14539* (2013.01); *A61B 5/14546* (2013.01); *A61B 5/6801* (2013.01); *A61B 5/0531* (2013.01); *A61B 5/7275* (2013.01); *A61B 2503/04* (2013.01); *A61B 2503/10* (2013.01); *A61B 2562/0219* (2013.01); *A61B 2562/14* (2013.01)

(58) Field of Classification Search
    USPC .................. 600/300–301, 307, 345–346
    See application file for complete search history.

(56) References Cited

U.S. PATENT DOCUMENTS

| | | | |
|---|---|---|---|
| 4,542,751 A | 9/1985 | Webster et al. | |
| 4,756,314 A | 7/1988 | Eckenhoff et al. | |
| 4,820,263 A | 4/1989 | Spevak et al. | |
| 5,036,861 A | 8/1991 | Sembrowich et al. | |
| 5,050,604 A | 9/1991 | Reshef et al. | |
| 5,140,985 A | 8/1992 | Schroeder et al. | |
| 5,246,003 A | 9/1993 | Delonzor | |
| 5,437,999 A | 8/1995 | Diebold et al. | |
| 5,438,984 A | 8/1995 | Schoendorfer | |
| 5,556,789 A | 9/1996 | Goerlach-Graw et al. | |
| 5,690,893 A | 11/1997 | Ozawa et al. | |
| 5,814,599 A | 9/1998 | Mitragotri et al. | |
| 5,944,662 A | 8/1999 | Schoendorfer | |
| 6,175,752 B1 | 1/2001 | Say et al. | |
| 6,198,953 B1 * | 3/2001 | Webster ............ A61N 1/30 | |
| | | | 600/345 |
| 6,256,533 B1 | 7/2001 | Yuzhakov et al. | |
| 6,269,265 B1 | 7/2001 | Anderson | |
| 6,299,578 B1 | 10/2001 | Kurnik et al. | |
| 6,592,529 B2 | 7/2003 | Marett | |
| 6,666,821 B2 | 12/2003 | Keimel | |
| 7,044,911 B2 | 5/2006 | Drinan et al. | |
| 7,190,986 B1 | 3/2007 | Hannula et al. | |
| 7,219,534 B2 | 5/2007 | Campbell | |
| 7,378,054 B2 | 5/2008 | Karmali | |
| 7,383,072 B2 | 6/2008 | Edmonson et al. | |
| 7,384,396 B2 | 6/2008 | Samuels et al. | |
| 7,703,336 B2 * | 4/2010 | Genosar ............ G01F 1/708 | |
| | | | 73/861.05 |
| 7,749,445 B2 | 7/2010 | Masters | |
| 7,800,494 B2 | 9/2010 | Kim | |
| 7,813,780 B2 | 10/2010 | Shah et al. | |
| 7,842,234 B2 | 11/2010 | Lauks et al. | |
| 7,959,791 B2 | 6/2011 | Kjaer et al. | |
| 8,125,539 B2 | 2/2012 | Takashima | |
| 8,128,889 B2 | 3/2012 | Fujimoto et al. | |
| 8,252,248 B2 | 8/2012 | Kramer | |
| 8,354,017 B2 | 1/2013 | Revol-Cavalier | |
| 8,391,946 B2 | 3/2013 | Sugenoya et al. | |
| 8,565,850 B2 | 10/2013 | Martinsen et al. | |
| 8,593,287 B2 | 11/2013 | Hayter et al. | |
| 8,617,067 B2 | 12/2013 | Jain et al. | |
| 9,133,024 B2 | 9/2015 | Phan et al. | |
| 9,603,560 B2 | 3/2017 | Monty et al. | |
| 9,867,539 B2 | 1/2018 | Heikenfeld et al. | |
| 2002/0091312 A1 | 7/2002 | Berner et al. | |
| 2003/0135100 A1 | 7/2003 | Kim et al. | |
| 2003/0201194 A1 | 10/2003 | Heller et al. | |
| 2004/0215098 A1 | 10/2004 | Barton et al. | |
| 2004/0249310 A1 | 12/2004 | Shartle et al. | |
| 2004/0260154 A1 | 12/2004 | Sidelnik et al. | |
| 2004/0267189 A1 | 12/2004 | Mavor et al. | |
| 2005/0042742 A1 | 2/2005 | Marett | |
| 2005/0069925 A1 | 3/2005 | Ford et al. | |
| 2005/0106713 A1 | 5/2005 | Phan et al. | |
| 2005/0177035 A1 | 8/2005 | Botvinick et al. | |
| 2005/0192528 A1 | 9/2005 | Tapper | |
| 2005/0197554 A1 | 9/2005 | Polcha | |
| 2005/0228297 A1 | 10/2005 | Banet et al. | |
| 2005/0280531 A1 | 12/2005 | Fadem et al. | |
| 2006/0009697 A1 | 1/2006 | Banet et al. | |
| 2006/0062852 A1 | 3/2006 | Holmes | |
| 2006/0127964 A1 | 6/2006 | Ford et al. | |
| 2006/0253011 A1 | 11/2006 | Edmonson et al. | |
| 2006/0254341 A1 | 11/2006 | Campbell | |
| 2007/0027383 A1 | 2/2007 | Peyser et al. | |
| 2007/0032731 A1 | 2/2007 | Lovejoy et al. | |
| 2007/0179371 A1 | 8/2007 | Peyser et al. | |
| 2008/0015494 A1 | 1/2008 | Santini, Jr. et al. | |
| 2008/0045816 A1 | 2/2008 | Jang et al. | |
| 2008/0154179 A1 | 6/2008 | Cantor et al. | |
| 2008/0214985 A1 | 9/2008 | Yanaki | |
| 2008/0286349 A1 | 11/2008 | Nomoto et al. | |
| 2008/0306362 A1 | 12/2008 | Davis | |
| 2009/0076345 A1 | 3/2009 | Manicka et al. | |
| 2009/0159442 A1 | 6/2009 | Collier et al. | |
| 2009/0173166 A1 * | 7/2009 | Genosar ............ G01F 1/708 | |
| | | | 73/861.05 |
| 2009/0204008 A1 | 8/2009 | Beilin | |
| 2009/0270704 A1 | 10/2009 | Peyser et al. | |
| 2010/0044224 A1 | 2/2010 | Kataky | |
| 2010/0063372 A1 | 3/2010 | Potts et al. | |
| 2010/0130843 A1 | 5/2010 | Caceres Galvez et al. | |
| 2010/0132485 A1 | 6/2010 | Erez et al. | |
| 2010/0198521 A1 | 8/2010 | Haick | |
| 2011/0004072 A1 | 1/2011 | Fletcher et al. | |
| 2011/0054273 A1 | 3/2011 | Omoda | |
| 2011/0079521 A1 | 4/2011 | Revol-Cavalier | |
| 2011/0118656 A1 | 5/2011 | Eckhoff et al. | |
| 2011/0178380 A1 | 7/2011 | Chowdhury | |
| 2011/0196283 A1 | 8/2011 | Imran et al. | |
| 2011/0208458 A1 | 8/2011 | Pinter et al. | |
| 2011/0275918 A1 | 11/2011 | Yamashita et al. | |
| 2012/0004570 A1 | 1/2012 | Shimizu et al. | |
| 2012/0028283 A1 | 2/2012 | Hoss et al. | |
| 2012/0119906 A1 | 5/2012 | Kountotsis | |
| 2012/0123220 A1 | 5/2012 | Iyer et al. | |
| 2012/0165626 A1 | 6/2012 | Irina et al. | |
| 2012/0191147 A1 | 7/2012 | Rao et al. | |
| 2012/0209226 A1 | 8/2012 | Simmons et al. | |
| 2012/0229661 A1 | 9/2012 | Sekiguchi et al. | |
| 2012/0245042 A1 * | 9/2012 | Liu ............ B01L 3/502723 | |
| | | | 506/7 |
| 2012/0277697 A1 | 11/2012 | Haghgooie et al. | |
| 2012/0285829 A1 | 11/2012 | Mount et al. | |
| 2012/0317430 A1 | 12/2012 | Rahman et al. | |
| 2013/0006079 A1 | 1/2013 | Feldman et al. | |
| 2013/0010108 A1 | 1/2013 | Hashizume et al. | |
| 2013/0013028 A1 | 1/2013 | Kriksunov et al. | |
| 2013/0053668 A1 | 2/2013 | Lin | |
| 2013/0079605 A1 | 3/2013 | Bandaru et al. | |
| 2013/0099937 A1 | 4/2013 | Azimi | |
| 2013/0108667 A1 | 5/2013 | Soikum et al. | |
| 2013/0123595 A1 | 5/2013 | Currie et al. | |
| 2013/0183399 A1 | 7/2013 | Blow et al. | |
| 2013/0245388 A1 | 9/2013 | Rafferty et al. | |
| 2013/0306491 A1 | 11/2013 | Briman et al. | |
| 2013/0317318 A1 | 11/2013 | Tartz et al. | |
| 2013/0317333 A1 | 11/2013 | Yang et al. | |
| 2014/0012114 A1 | 1/2014 | Zevenbergen et al. | |
| 2014/0025000 A1 | 1/2014 | Currie et al. | |
| 2014/0206977 A1 | 7/2014 | Bahney et al. | |
| 2014/0221792 A1 | 8/2014 | Miller et al. | |

(56) References Cited

U.S. PATENT DOCUMENTS

| | | | |
|---|---|---|---|
| 2014/0275862 A1 | 9/2014 | Kennedy | |
| 2014/0276220 A1 | 9/2014 | Briscoe et al. | |
| 2014/0343371 A1 | 11/2014 | Sowers, II et al. | |
| 2015/0057515 A1 | 2/2015 | Hagen et al. | |
| 2015/0112164 A1 | 4/2015 | Heikenfeld et al. | |
| 2015/0112165 A1 | 4/2015 | Heikenfeld | |
| 2015/0289820 A1 | 4/2015 | Miller et al. | |
| 2015/0204763 A1* | 7/2015 | Stelzle | B01L 3/502715 435/6.11 |
| 2016/0058354 A1 | 3/2016 | Phan et al. | |
| 2016/0066828 A1 | 3/2016 | Phan et al. | |
| 2016/0157768 A1 | 6/2016 | Braig et al. | |
| 2016/0287164 A1* | 10/2016 | Manion | G01F 25/0007 |
| 2016/0290952 A1* | 10/2016 | Pizer | H05K 3/10 |
| 2017/0100035 A1 | 4/2017 | Heikenfeld | |
| 2017/0100071 A1 | 4/2017 | Heikenfeld | |
| 2017/0172470 A1 | 6/2017 | Begtrup et al. | |
| 2017/0215773 A1 | 8/2017 | Heikenfeld et al. | |

FOREIGN PATENT DOCUMENTS

| | | | | |
|---|---|---|---|---|
| EP | 1575010 | A1 | 9/2005 | |
| EP | 1637889 | A1 | 3/2006 | |
| EP | 2551784 | A1 | 1/2013 | |
| EP | 2783725 | A1 | 10/2014 | |
| WO | 1990011519 | A1 | 10/1990 | |
| WO | 1994014062 | A1 | 6/1994 | |
| WO | 2000014535 | A1 | 3/2000 | |
| WO | 2001088525 | A1 | 11/2001 | |
| WO | 2006133101 | A2 | 12/2006 | |
| WO | 2007097754 | A1 | 8/2007 | |
| WO | 2007146047 | A1 | 12/2007 | |
| WO | 2008058014 | A2 | 5/2008 | |
| WO | 2008083687 | A1 | 7/2008 | |
| WO | 2008095940 | A1 | 8/2008 | |
| WO | 2009004001 | A1 | 1/2009 | |
| WO | 2009052321 | A2 | 4/2009 | |
| WO | 2010017578 | A1 | 2/2010 | |
| WO | 2011008581 | A2 | 1/2011 | |
| WO | 2011117952 | A1 | 9/2011 | |
| WO | 2013111409 | A1 | 8/2013 | |
| WO | 2013181436 | A1 | 12/2013 | |
| WO | 2014001577 | A1 | 1/2014 | |
| WO | 2014025430 | A2 | 2/2014 | |
| WO | 2015058065 | A1 | 4/2015 | |
| WO | 2016007944 | A2 | 1/2016 | |
| WO | 2016049019 | A1 | 3/2016 | |
| WO | 2016090189 | A1 | 6/2016 | |
| WO | 2016130905 | A1 | 8/2016 | |
| WO | 2016138087 | A1 | 9/2016 | |
| WO | WO 2016180964 A1 * | | 11/2016 | G01N 11/04 |
| WO | 2017019602 | A1 | 2/2017 | |
| WO | 2017070640 | A1 | 4/2017 | |

OTHER PUBLICATIONS

Kuo, Jonathan TW, Lawrence Yu, and Ellis Meng. "Micromachined thermal flow sensors—A review." Micromachines 3.3 (2012): 550-573. doi:10.3390/mi3030550.*

European Patent Office, Supplemental European Search Report issued in European Application No. 15799317.1-1657 dated Dec. 21, 2017, 9 pages.

International Bureau, Written Opinion of the International Searching Authoring/International Preliminary Report on Patentability for PCT/US2013/035092 dated Oct. 16, 2014 (14 pages).

Baker, et al., "Comparison of regional patch collection vs. whole body washdown for mesuring sweat sodium and potassium loss during exercise", The American Physiological Society, pp. 887-895, 2009.

Fu et al, "Controlled Reagent Transport in Disposable 2D Paper Networks", The Royal Society of Chemistry 2010, Lab Chip, 2010, 10, 918-920.

Heikenfeld, J., "Let Them See You Sweat", IEEE Spectrum, pp. 46-50 and 62-63, Nov. 2014.

Pike, Douglas J., et al., "Flow Cell Design for Effective Biosensing," Sensors, ISSN 1424-8220, Dec. 2012, vol. 13, pp. 58-70, www.mdpi.com/journal/sensors, 13 pages.

Rose, et al., "Adhesive RFID Sensor Patch for Monitoring of Sweat Electrolytes", IEEE Transactions on Biomedical Engineering, pp. 1-9, 2013.

Saini, Vipin, et al., "Non Invasive Therapeutic Drug Monitoring of Propranolol Hydrochloride by Reverse Iontophoresis," International Research Journal of Pharmacy, 2012, vol. 3(4), pp. 395-399 (6 pages).

Sonner, Z., et al., "The microfluidics of the eccrine sweat gland, including biomarker partition, transport, and biosensing implications,"Biomicrofluidics, vol. 9, pp. 031301-1-031301-19, CrossMark, 19 pages.

Stoppa, Matteo, et. al., "Wearable Electronics and Smart Textiles: A Critical Review," Sensors, 2014, pp. 11957-11992, vol. 14 (36 pages).

Taylor, et al., "Regional variations in transepidermal water loss, eccrine sweat gland density, sweat secretion rates and electrolyte composition in resting and exercising humans", Extreme Physiology & Medicine, vol. 2, No. 4, pp. 1-29, 2013.

European Patent Application No. EP15790344.4, Office Action, dated Oct. 6, 2017, 8 pages.

European Patent Application No. EP17172694.6 Extended European Search Report, dated Oct. 11, 2017, 8 pages.

International Search Report issued in International Patent Application No. PCT/US2013/035092, dated Dec. 3, 2013, 7 pages.

European Patent Office, Partial European Search Report issued in European Application No. 15800043.0-115 dated Jan. 8, 2018, 13 pages.

European Patent Office, Supplemental European Search Report issued in European Application No. 15799514.3-1657 dated Dec. 7, 2017, 8 pages.

European Patent Office, Partial European Search Report issued in European Application No. 16203346.8-1657 dated Mar. 24, 2017, 7 pages.

International Bureau, Annex to Invitation to Pay Additional Fees issued in International Application No. PCT/US2013/035092, dated Aug. 26, 2013 (9 pages).

International Searching Authority, Search Report and Written Opinion issued in corresponding International Application No. PCT/US2017/042677 dated Nov. 17, 2017, 13 pages.

International Searching Authority, Search Report and Written Opinion issued in corresponding International Application No. PCT/US2015/055756 dated Apr. 8, 2016, 17 pages.

International Searching Authority, Annex to Invitation to Pay Additional Fees issued in corresponding International Application No. PCT/US2015/055756 dated Jan. 26, 2016, 8 pages.

International Searching Authority, Search Report and Written Opinion issued in corresponding International Application No. PCT/US2016/019282 dated Jul. 27, 2016, 18 pages.

International Searching Authority, Annex to Invitation to Pay Additional Fees issued in corresponding International Application No. PCT/US2016/019282 dated May 11, 2016, 5 pages.

International Searching Authority, Search Report and Written Opinion issued in corresponding International Application No. PCT/US2016/036038 dated Oct. 14, 2016, 13 pages.

International Searching Authority, Search Report and Written Opinion issued in corresponding International Application No. PCT/US2016/035972 dated Oct. 4, 2016, 11 pages.

International Searching Authority, Annex to Invitation to Pay Additional Fees issued in corresponding International Application No. PCT/US2016/035972 dated Jul. 28, 2016, 3 pages.

International Searching Authority, Search Report and Written Opinion issued in corresponding International Application No. PCT/US2016/043771 dated Dec. 8, 2016, 13 pages.

International Searching Authority, Search Report and Written Opinion issued in corresponding International Application No. PCT/US2016/053625 dated Dec. 8, 2016, 14 pages.

(56) References Cited

OTHER PUBLICATIONS

International Searching Authority, Search Report and Written Opinion issued in corresponding International Application No. PCT/US2016/058356 dated Jan. 6, 2017, 15 pages.
International Searching Authority, Search Report and Written Opinion issued in corresponding International Application No. PCT/US2017/021503 dated Jul. 10, 2017, 14 pages.
International Searching Authority, Search Report and Written Opinion issued in corresponding International Application No. PCT/US2017/023399 dated Jul. 3, 2017, 10 pages.
International Searching Authority, Search Report and Written Opinion issued in corresponding International Application No. PCT/US2016/058357 dated Jan. 19, 2017, 9 pages.
International Searching Authority, Search Report and Written Opinion issued in corresponding International Application No. PCT/US2017/045926 dated Oct. 31, 2017, 12 pages.
International Searching Authority, Search Report and Written Opinion issued in corresponding International Application No. PCT/US2017/045121 dated Oct. 20, 2017, 12 pages.
International Searching Authority, Search Report and Written Opinion issued in corresponding International Application No. PCT/US2017/058281 dated Jan. 17, 2018, 10 pages.
International Searching Authority, Search Report and Written Opinion issued in corresponding International Application No. PCT/US2017/047808 dated Nov. 6, 2017, 10 pages.
International Search Report issued in International Patent Application No. PCT/US2017/042677, dated Jan. 31, 2019, 10 pages.

* cited by examiner

SWEAT CONDUCTIVITY, VOLUMETRIC SWEAT RATE, AND GALVANIC SKIN RESPONSE DEVICES AND APPLICATIONS

CROSS-REFERENCE TO RELATED APPLICATIONS

This application relates to U.S. Provisional Application No. 62/364,034, filed Jul. 19, 2016; U.S. Provisional Application No. 62/464,610, filed Feb. 28, 2017; U.S. Provisional Application No. 62/510,491, filed May 24, 2017; and has specification that builds upon PCT/US16/36038, filed Jun. 6, 2016, the disclosures of which are hereby incorporated herein by reference in their entirety.

BACKGROUND OF THE INVENTION

Sweat sensing technologies have enormous potential for applications ranging from athletics, to neonatology, to pharmacological monitoring, to personal digital health, to name a few applications. This is because sweat contains many of the same biomarkers, chemicals, or solutes that are carried in blood, which can provide significant information enabling the diagnosis of ailments, health status, toxins, performance, and other physiological attributes even in advance of any physical sign. Furthermore, sweat itself, and the action of sweating, or other parameters, attributes, solutes, or features on or near skin or beneath the skin, can be measured to further reveal physiological information.

In particular, sweat sensing devices hold tremendous promise for use in workplace safety, athletic, military, and clinical diagnostic settings. A primary goal of the disclosed invention is to provide decision support to a sweat sensor system user that is informative at the level of the individual patient. A sweat sensing device worn on the skin and connected to a computer network via a reader device, such as a smart phone or other portable or stationary computing device, could aid in recognition of the physiological state of an individual, and relay crucial data about physiological states. In certain settings, sweat sensing devices may continuously monitor certain aspects of an individual's physiological state and communicate relevant information to a reader device or computer network, which would then compare collected data to threshold readings and generate notification messages to the individual, a caregiver, a work supervisor, or other device user. For example, an individual's sweat ion content could be indicated by directing a sweat sample flow across a plurality of electrodes that are configured to measure sweat conductivity; the individual's sweat onset and cessation can be indicated by measuring galvanic skin response ("GSR"); and the individual's sweat rate can be indicated by directing a sweat sample through a channel of defined volume containing a plurality of sweat-activated electrode switches. These three capabilities can be combined in a single device, which can use a volumetric sweat rate sensor to calibrate the individual's sweat conductivity and GSR measurements, and thereby provide useful information about the individual's physiological state, including sweat rate, sweat content, water loss, and dehydration state. The scope of the disclosed invention therefore comprises wearable devices configured to measure sweat conductivity, GSR, and/or volumetric sweat rate, devices that use volumetric sweat rate to calibrate, improve, and extend sweat conductivity and GSR measurements, and methods to accompany the use of such devices.

Definitions

Before continuing with the background, a variety of definitions should be made, these definitions gaining further appreciation and scope in the detailed description and embodiments of the present invention.

As used herein, "sweat" means a biofluid that is primarily sweat, such as eccrine or apocrine sweat, and may also include mixtures of biofluids such as sweat and blood, or sweat and interstitial fluid, so long as advective transport of the biofluid mixtures (e.g., flow) is primarily driven by sweat.

"Sweat sensor" means any type of sensor that measures a state, presence, flow rate, solute concentration, or solute presence, in absolute, relative, trending, or other ways in sweat. Sweat sensors can include, for example, potentiometric, amperometric, impedance, optical, mechanical, antibody, peptide, aptamer, or other means known by those skilled in the art of sensing or biosensing.

"Analyte" means a substance, molecule, ion, or other material that is measured by a sweat sensing device.

"Measured" can imply an exact or precise quantitative measurement and can include broader meanings such as, for example, measuring a relative amount of change of something. Measured can also imply a qualitative measurement, such as 'yes' or 'no' type measurements.

"Chronological assurance" means the sampling rate or sampling interval that assures measurement(s) of analytes in sweat in terms of the rate at which measurements can be made of new sweat analytes emerging from the body. Chronological assurance may also include a determination of the effect of sensor function, potential contamination with previously generated analytes, other fluids, or other measurement contamination sources for the measurement(s). Chronological assurance may have an offset for time delays in the body (e.g., a well-known 5 to 30-minute lag time between analytes in blood emerging in interstitial fluid), but the resulting sampling interval (defined below) is independent of lag time, and furthermore, this lag time is inside the body, and therefore, for chronological assurance as defined above and interpreted herein, this lag time does not apply.

"Analyte-specific sensor" means a sensor specific to an analyte and performs specific chemical recognition of the analyte's presence or concentration (e.g., ion-selective electrodes ("ISE"), enzymatic sensors, electro-chemical aptamer based sensors, etc.). Sensors could also be optical, mechanical, or use other physical/chemical methods which are specific to a single analyte. Further, multiple sensors can each be specific to one of multiple analytes.

"Sweat sensor data" means all of the information collected by sweat system sensor(s) and communicated via the system to a user or a data aggregation location.

"Correlated aggregated sweat sensor data" means sweat sensor data that has been collected in a data aggregation location and correlated with outside information such as time, temperature, weather, location, user profile, other sweat sensor data, or any other relevant data.

"Sweat conductivity" means measurements of the electrical conductivity of sweat. Sweat conductivity serves as a means of estimating $Na^+$ and $Cl^-$ content, since $Cl^-$ represents the dominant anion in sweat, and is usually paired with $Na^+$ as salt. However, conductivity does not precisely correlate to $Cl^-$ levels, because lactate and bicarbonate also make significant contributions to sweat conductivity. The sweat sensing device measures sweat conductivity by means of an electrode.

"Galvanic skin response" ("GSR") means measurements of the electrical conductivity of the skin. GSR serves as a means of determining sweat onset and cessation, and can be used to estimate sweat rate, since skin conductivity is dominated by the contribution of sweat, and increases linearly with increases in sweat rate throughout the linear range of 0.4 µL/cm²/min to 1.5 µL/cm²/min.

"Volumetric sweat rate measurement" means a measurement of sweat rate based on the time required for sweat to fill a known volume in a sweat sensing device.

This has served as a background for the present invention, including background technical invention needed to fully appreciate the present invention, which will now be summarized.

SUMMARY OF THE INVENTION

The disclosure provides: sweat sensing devices configured to periodically measure sweat conductivity and galvanic skin response, devices to measure volumetric sweat flow rate, and devices that combine the three functions. The disclosure further includes methods for using a device configured to perform periodic sweat conductivity measurements, galvanic skin response measurements, and volumetric sweat rate measurements so that each sensor modality informs composite estimates of sweat onset, sweat cessation, sweat ion concentration, and sweat rate. The method uses those measurements to inform other sweat sensing device functions, such as determining the existence of a physiological condition, or performing measurements of concentrations, ratios, and trends of sweat analytes.

BRIEF DESCRIPTION OF THE DRAWINGS

The objects and advantages of the present invention will be further appreciated in light of the following detailed descriptions and drawings in which.

DETAILED DESCRIPTION OF THE INVENTION

The detailed description of the present invention will be primarily, but not entirely, limited to devices, methods and sub-methods using wearable sweat sensing devices. Therefore, although not described in detail here, other essential steps which are readily interpreted from or incorporated along with the present invention shall be included as part of the disclosed invention. The disclosure provides specific examples to portray inventive steps, but which will not necessarily cover all possible embodiments commonly known to those skilled in the art. For example, the specific invention will not necessarily include all obvious features needed for operation. Several specific, but non-limiting, examples can be provided as follows. The disclosed invention incorporates by reference in their entirety the article published in the journal *IEEE Transactions on Biomedical Engineering*, titled "Adhesive RFID Sensor Patch for Monitoring of Sweat Electrolytes"; and the article published in the journal *AIP Biomicrofluidics*, 9 031301 (2015), titled "The Microfluidics of the Eccrine Sweat Gland, Including Biomarker Partitioning, Transport, and Biosensing Implications".

Figure 1:
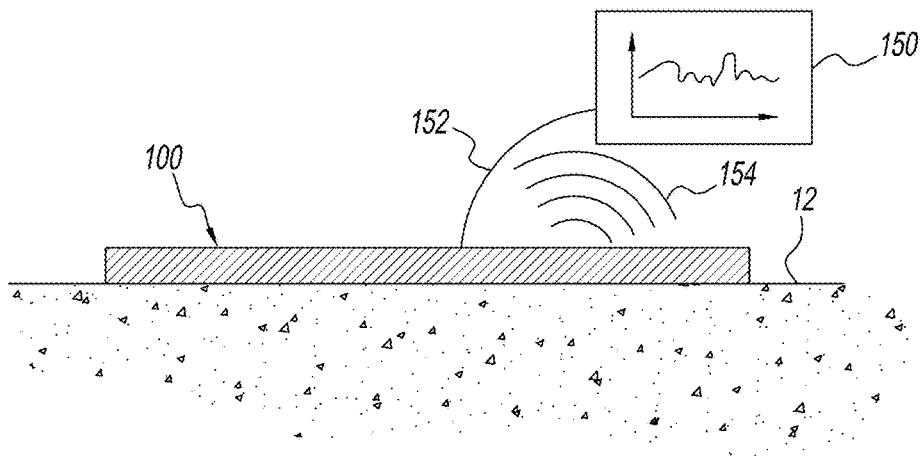
FIG. 1 is an example sweat sensing device of the present disclosure.

With reference to FIG. 1, a representative sweat sensing device 1 for use with the present disclosed invention is placed on or near skin 12. The sweat sensing device may be fluidically connected to skin or regions near skin through microfluidics or other suitable techniques. The device 1 is in wired communication 110 or wireless communication 120 with a reader device 130, which could be a smart phone or portable electronic device, or for some devices, the device 1 and reader device 130 can be combined. Communication 110 or 120 is not necessarily constant and could be a simple one-time data download from the device once the device has completed its measurements of sweat.

The sweat sensing device may include a plurality of sensors to detect and improve detection of sweat analytes, including ISEs, a reference electrode, a pH sensor, a temperature sensor, a skin impedance sensor, a capacitive skin proximity sensor, and an accelerometer. Many of the auxiliary features of the invention may require other aspects of a sweat sensing device, including two or more counter electrodes, reference electrodes, or additional supporting technology or features, which are not captured in the description herein, such as an onboard real-time clock, onboard flash memory (i.e., 1 MB minimum), Bluetooth™ or other communications hardware, and a multiplexer to process a plurality of sensor outputs.

The sweat sensing device also includes computing and data storage capability sufficient to operate the device, which incorporates the ability to conduct communication among system components, to perform data aggregation, and to execute algorithms capable of generating notification messages. The device may have varying degrees of onboard computing capability (i.e., processing and data storage capacity). For example, all computing resources could be located onboard the device, or some computing resources could be located on a disposable portion of the device and additional processing capability located on a reusable portion of the device. Alternatively, the device may rely on portable, fixed or cloud-based computing resources.

The sweat sensing device's data aggregation capability may include collecting all of the sweat sensor data generated by sweat sensing devices and communicated to the device. The aggregated sweat sensor data could be de-identified from individual wearers, or could remain associated with an individual wearer. Such data can also be correlated with outside information, such as the time, date, air temperature, humidity, activity performed by the individual, motion level, fitness level, mental and physical performance during the data collection, body orientation, the proximity to significant health events or stressors, age, sex, medications, drug sensitivity, medical condition, health history, or other relevant information. The reader device or companion transceiver can also be configured to correlate speed, location, environmental temperature or other relevant data with the sweat sensor data. The data collected could be made accessible via secure website portal to allow sweat system users to perform safety, compliance and/or care monitoring of target individuals. The sweat sensor data monitored by the user includes real-time data, trend data, or may also include aggregated sweat sensor data drawn from the system database and correlated to a particular user, a user profile (such as age, sex or fitness level), weather condition, activity, combined analyte profile, or other relevant metric. Trend data, such as a target individual's hydration level over time, could be used to predict future performance, or the likelihood of an impending physiological event. Such predictive capability can be enhanced by using correlated aggregated data, which would allow the user to compare an individual's historical analyte and external data profiles to a real-time situation as it progresses, or even to compare thousands of similar analyte and external data profiles from other individuals to the real-time situation. Sweat sensor data may also be used to identify wearers that are in need of additional monitoring or instruction, such as the need to drink additional water, or to adhere to a drug regimen.

Sweat is known to contain a large number of molecules that could be used to indicate an individual's physiological state. In general, determining an individual's physiological state is a significant challenge. Not only is every individual different in terms of how a physiological state may present, but even a simple physiological state or disorder is a complex set of biological processes that does not readily lend itself to reduction. Consequently, a definitive diagnosis of a physiological condition often is not possible. One solution is to divide individuals according to phenotypes or susceptibilities that indicate the mode in which a physiological state is likely to manifest in those individuals. These phenotypes may be indicated by analyte signatures that emerge in sweat. To date, there have been only a few studies—such as those linking sweat chloride and cystic fibrosis—examining the relationships between sweat analytes and physiological states. It is therefore necessary to build data across multiple individuals correlating physiological states with sweat analyte readings. By this means, discernable sweat analyte signatures are identified that provide useful information about a given physiological state.

Further, this translation of analyte concentrations and ratios to meaningful physiological information accounts for a number of variabilities unrelated to differences in concentrations. For example, sweat concentrations of analytes relative to blood or plasma concentrations are known to vary depending on sweat rate, the body location from which a sample is taken, kidney or liver disease or function, external temperatures, and other factors. Therefore, algorithms and techniques are required to adjust sweat analyte signatures to account for these variabilities.

In this context, sweat rate is an important metric that can inform many sweat sensing device applications, e.g., ensuring sweat conductivity measurements are only taken at chronologically assured sweat sampling rates. For the purposes of the disclosed invention, volumetric sweat rate measurements are used to calibrate and inform sweat conductivity readings and GSR. For example, changes in GSR readings consist of three major components: sweat rate, sweat ion content (conductivity), and skin contact resistance. The independent measure of sweat rate provided by the volumetric sensor can therefore inform the sweat rate component of GSR, allowing more accurate estimates of the remaining two components. Further, volumetric sensor measurements improve and extend sweat rate estimates derived from sweat conductivity measurements.

Figure 2:
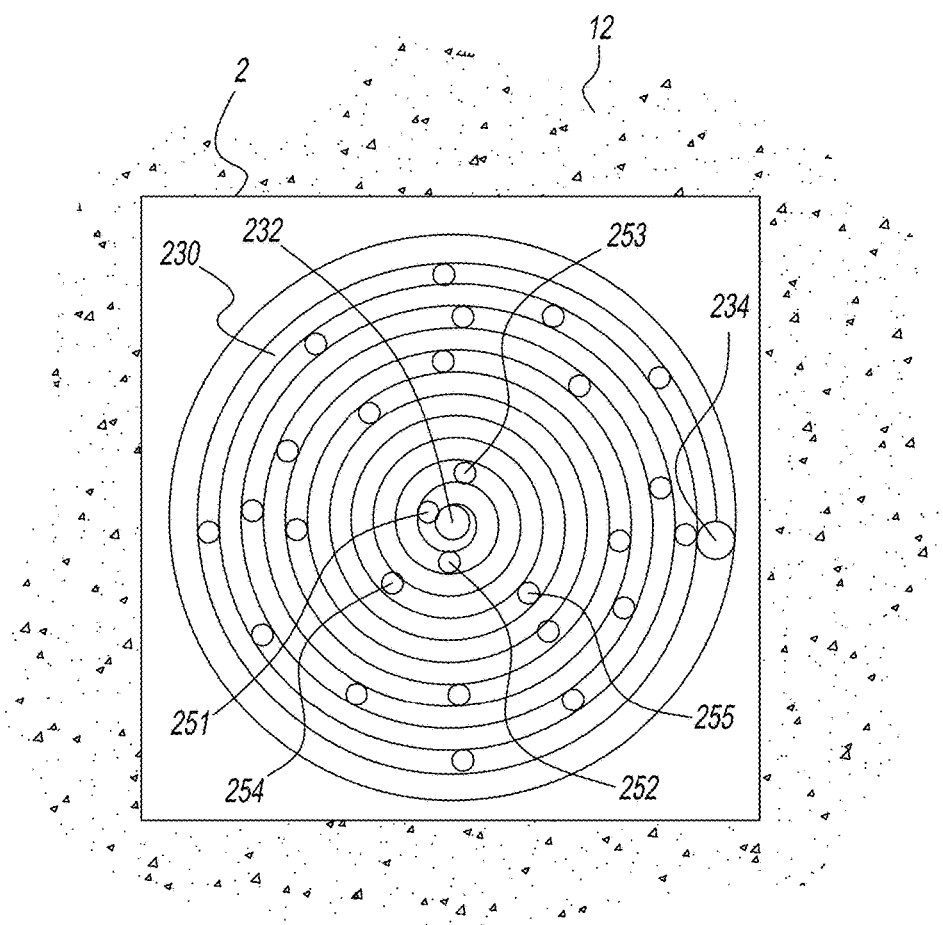
FIG. 2 represents at least a portion of an embodiment of the disclosed invention configured to measure volumetric sweat rate.

The disclosed sweat sensing device will therefore include a volumetric sweat rate sensor that is configured to determine sweat rate by periodically detecting a sweat sample as it fills known volumes within a microfluidic channel. Such measurements provide a sweat flow rate, and a sweat generation rate from the skin under the device as disclosed in U.S. Provisional No. 62/464,610, filed Feb. 28, 2017, hereby incorporated by reference herein in its entirety. With reference to FIG. 2, a sweat sensing device 2 capable of volumetric sweat rate measurement is placed on skin 12. The sweat rate sensor includes a microfluidic channel 230, shown here arranged in a spiral pattern to maximize available volume for a given surface area, and a plurality of electrodes 251, 252, 253, 254, 255 (several are shown). The channel 230 has a volume, e.g., several nL. The channel volume is chosen based on the requirements of the application, for example, a larger volume channel may be used where high sweat rates are anticipated. Alternately, the channel volume may be determined by the duration a device must operate, e.g., 2 hours, 8 hours, 24 hours, or longer. The channel cross-section may also vary along its length to achieve a chosen volume in a section of the channel. In some embodiments, the channel cross-section will be small enough to facilitate capillary action wicking pressure that will at least partially draw the sweat sample through the channel. Other embodiments will rely on positive pressure from sweat generation to drive the sample through the channel. Some embodiments will include air traps or air bubble venting components to prevent air bubbles from interfering with measurements taken by electrodes or other sensors.

The electrodes 251, 252, 253, 254, 255 are placed within the channel at selected distances from each other, so that the channel volumes between electrodes are determined, e.g., several nL. Electrode spacing can be chosen to suit the particular application. For example, the device may include several closely-spaced electrodes in a first portion of the channel, and several more distantly-spaced electrodes in a second portion of the channel. Such a configuration could accommodate a wide range of sweat rates, so that at low sweat rates, the closely-spaced electrodes would provide useful data, and at higher sweat rates, the distantly-spaced electrodes would provide useful data. Different combinations of varied electrode spacing and channel volumes are possible and contemplated within the present disclosure.

During device operation, when the wearer begins to sweat, a sweat sample will move into the device at the inlet 232, into the microfluidic channel 230, and will contact the first electrode 251. When sweat reaches the electrode 251, the device will detect a current, which will register as a potential relative to an electrical ground. As sweat reaches each subsequent electrode 252, 253, 254, 255, the device will detect a potential at the electrode relative to ground. The rate at which additional electrodes register a potential, coupled with the volume of the channel section that is filled with sweat, will provide a sweat rate value. If the sweat sample completely fills the channel 230, excess sweat will then be transported into a sweat collecting pump or reservoir (not shown), or passed out of the device at a drain 234. In another embodiment, the first electrode 251 is a reference electrode, and as sweat reaches each subsequent electrode 252, 253, 254, 255, a detection circuit will be completed between the reference electrode and the subsequent electrodes.

Figure 3:
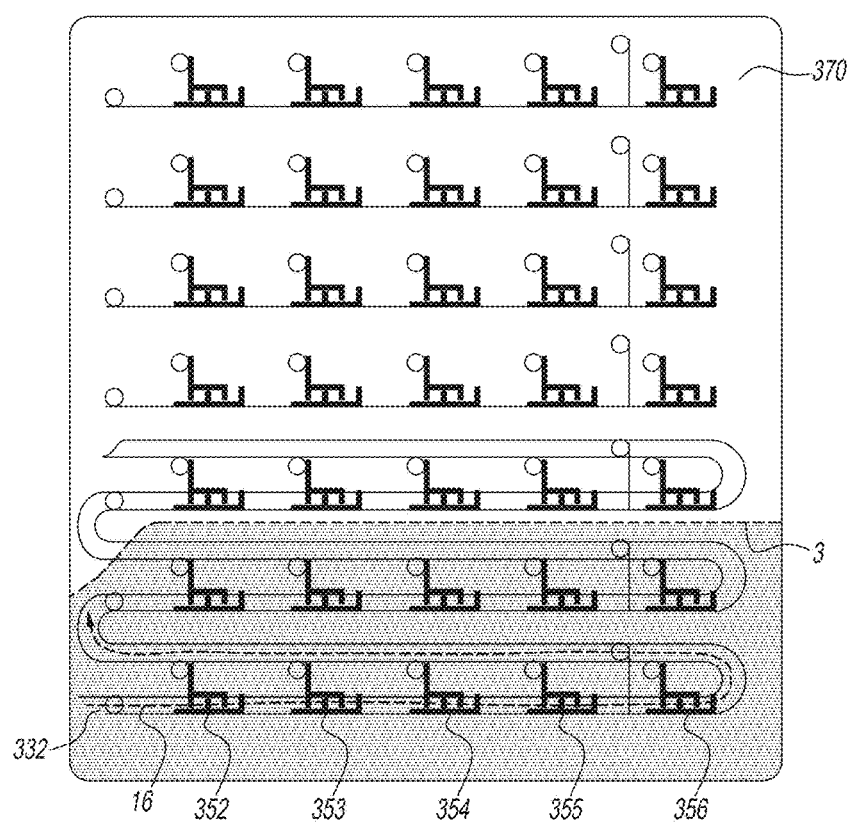
FIG. 3 represents at least a portion of an embodiment of the disclosed invention configured to measure volumetric sweat rate.

With reference to FIG. 3, another sweat sensing device 3 capable of volumetric sweat rate measurement is placed on skin 12. The device includes a plurality of interdigitated electrode switches 352, 353, 354, 355, 356 that are arranged on a substrate 370, such as a printed circuit board, to correspond to a microfluidic channel 330. The switches are placed along the channel, with a first switch 352 being located at or near an inlet 332, and the remaining switches 353, 354, 355 placed at selected distances from each other thereafter, so that the channel volumes between switches are determined, e.g., 1-5 nL. Channel volume and switch spacing can be adjusted to suit the application, and different combinations of varied switch spacing, channel volumes and collection areas are possible and contemplated.

Figure 3A:
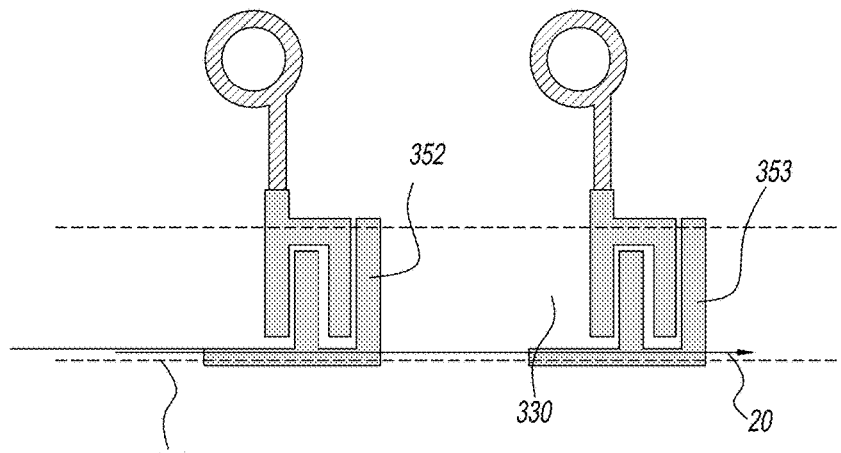
FIGS. 3A and 3B represent close-up views of at least a portion of the device depicted in FIG. 3.
Figure 3B:
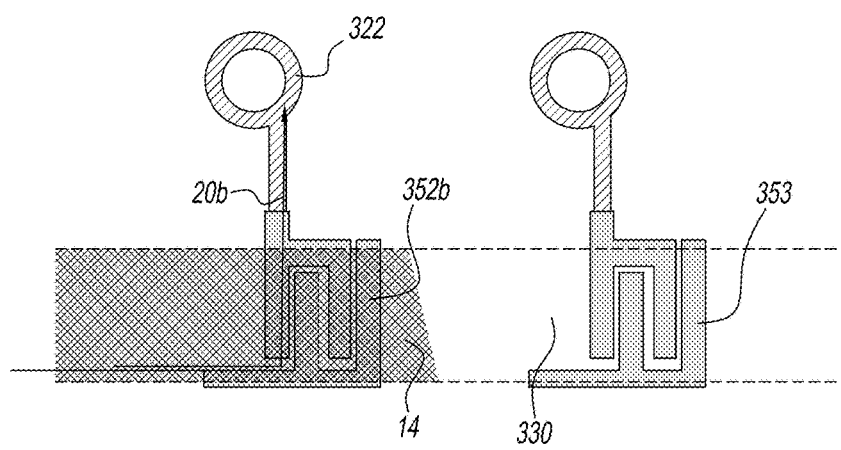

The figure includes a separate layer that carries the microfluidic channel 330, which is depicted as cut away along the dotted line 3. However, some embodiments may use a microfluidic textile or wick rather than the channel as shown. Each switch comprises a set of interdigitated electrodes, which reroute electrical current in the presence of sweat. The switches are wired as an array, so that when the switch is dry (or open), current flows through a resistor circuit, but when the interdigitated electrodes are electrically connected by the sweat sample, the switch is closed. Upon switch closure, current bypasses the resistor circuit and enters a ground circuit, which the device interprets as the presence of sweat at the switch. With reference to FIG. 3A, a close-up view of the switches 352, 353 is depicted, along with a depiction of the microfluidic channel path 330 in relation to the switches. The switches are wired together in a matrix by embedded circuitry 320. When the switches are dry, current will bypass the switches and flow in the direction of the arrow 20. However, as depicted in FIG. 3B, when a sweat sample 14 enters the channel 330, and contacts a switch 352b, current 20b will enter the switch and flow toward the ground circuit 322. The device then interprets a signal at the ground circuit associated with the closed switch 352B as indicative of the presence of sweat.

With further reference to FIG. 3, as a sweat sample flows into the channel 330 along the serpentine path depicted by the arrow 16, it encounters each switch in succession. While the path depicted here is serpentine, the invention is not so limited, and could be, e.g., a spiral, leading edge, or other suitable pattern. The rate at which additional switches are closed by the sweat sample, coupled with the volume of the channel section that is filled with sweat, provides a sweat rate value. Because of space limitations on the wearable device, volumetric sweat rate channels have limited operational lifespans that may not cover an entire application period. For example, at moderately high sweat rates, i.e., 10 nL/min/gland, a device as disclosed having a sweat collection area of about 2 cm$^2$ would operate for about 2 hours. The channel design can be modified to facilitate individual applications by varying channel geometry (length, cross section, path geometry), inner surface treatments, or switch spacing. For example, for high sweat rate individuals or applications, the channel has a 2× to 4× greater cross section to increase the available volume between switches, which would increase channel lifetime by 2× to 4×, respectively. Other embodiments include a sweat collecting pump or reservoir (not shown), or include a drain (not shown) to pass sweat out of the device.

Figure 4:
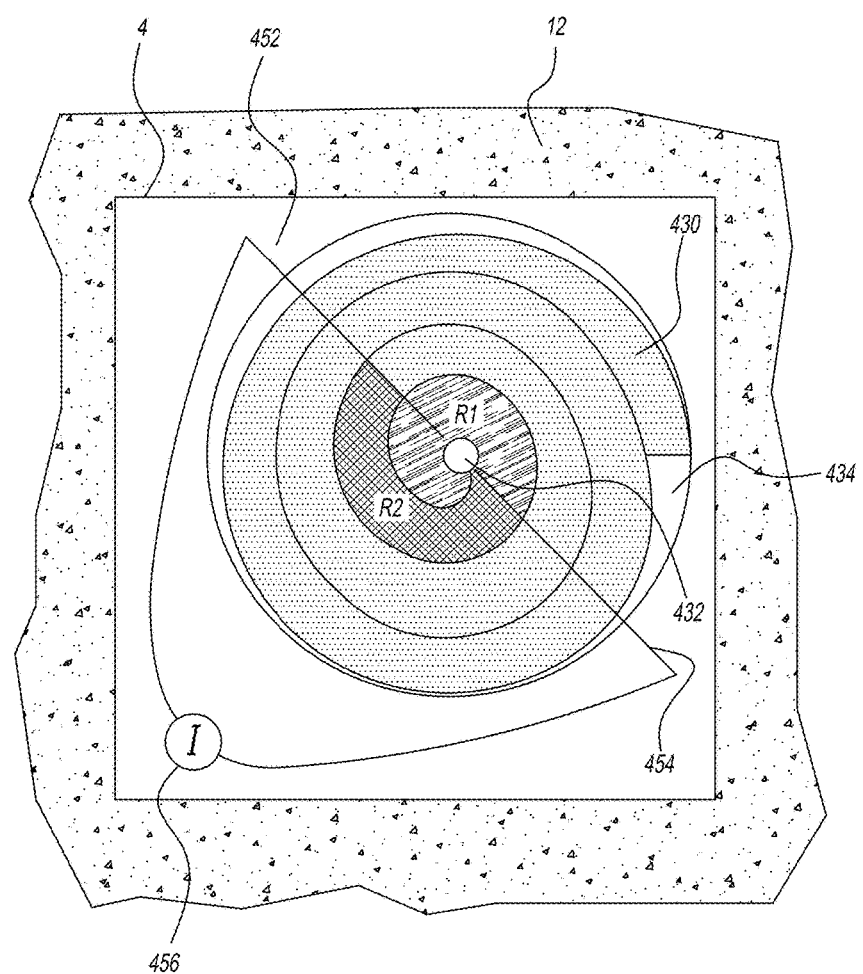
FIG. 4 represents at least a portion of an embodiment of the disclosed invention configured to measure volumetric sweat rate.

With reference to FIG. 4, where like numbers refer to like components depicted in previous figures, an alternative embodiment of the disclosed invention includes a simpler design for measuring sweat rate. Having a plurality of separate electrodes as described in FIG. 2 would require separate treatment and multiplexing by the device's electronics, substantially limiting the number of electrodes that may be used. The alternate embodiment depicted instead includes a plurality of linear electrodes, for example two electrodes 452, 454, aligned perpendicularly to the channel cross sections. The channel 430 will have determined volumes in between the points where an electrode intersects with the channel cross-section. In operation, a sweat sample moves into the channel 430 at the inlet 432, where the sweat sample will contact the first electrode 452. As sweat continues to fill the channel 430, it will contact the second electrode 454, completing a detection circuit 456, and causing the device to register a current according to Ohm's law, $$I = \frac{V}{R_1},$$

where $R_1$ is the resistance of the first channel section between the electrodes that is filled with sweat. As the sweat sample continues to fill the channel 430, it will again contact the first electrode 452, completing a circuit that now includes a second section of the channel that is filled with sweat. Now the device will register an increased current, because the two channel sections act as resistors wired in parallel, which lowers the overall resistance, thereby increasing the current, e.g., $$I = \frac{V}{\frac{1}{\left(\frac{1}{R_1} + \frac{1}{R_2}\right)}},$$

where $R_2$ is the resistance of the second channel section filled with sweat. Sweat rate will be determined by measuring the time required to fill each determined volume of the channel, as indicated by a detected increase in current flowing through the circuit 456.

Ohm's law also provides that each sweat filled channel section added to the circuit (assuming they have equal resistance) will have a proportionally smaller impact on the circuit. Therefore, as channel sections are added, the voltage step will gradually decrease to zero, creating an upper limit for the number of channel sections that can be used in the device. To counteract this tendency, the resistance for each additional channel increases, preferably on a logarithmic scale, over the previous channel so that the new resistor has a proportional impact on the overall circuit. In the embodiment depicted in FIG. 4, each successive channel section is longer than the previous section, and therefore will possess a greater resistance. The effective resistance for each channel section can also be increased by adjusting the resistance of the electrode traces that connect each section to the circuit.

Figure 5:
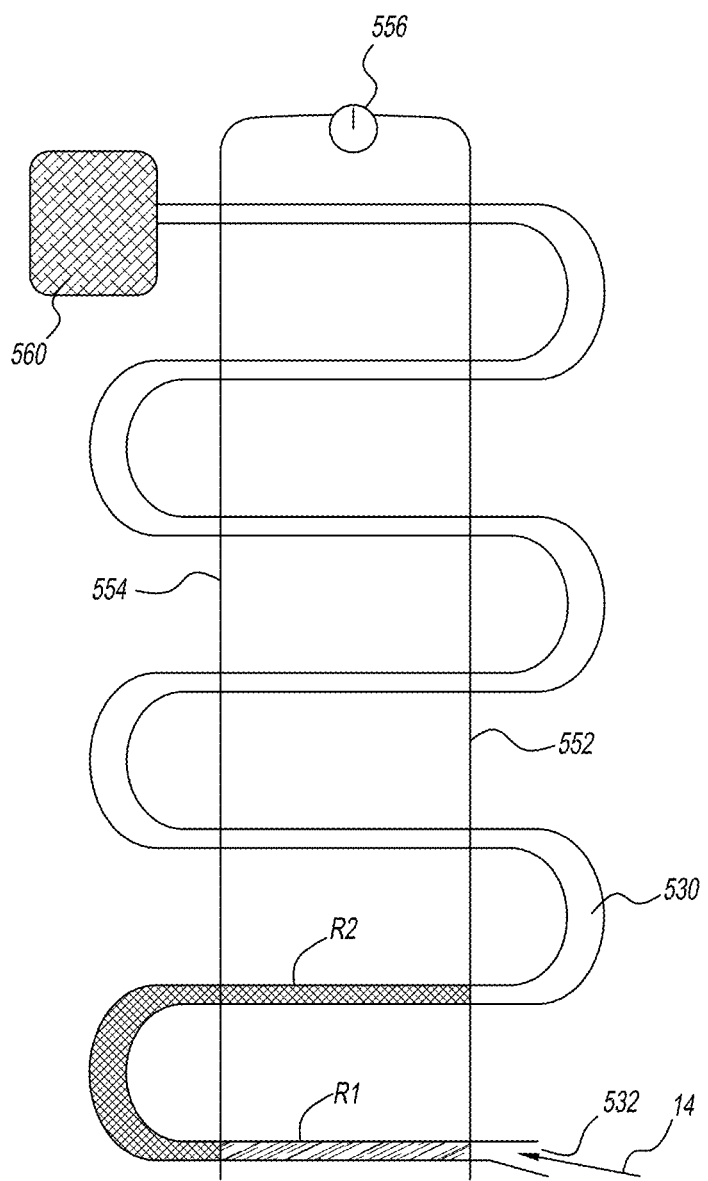
FIG. 5 represents at least a portion of an embodiment of the disclosed invention configured to measure volumetric sweat rate.

With reference to FIG. 5, where like numbers refer to like components depicted in previous figures, in another embodiment, the microfluidic channel has a serpentine, rather than a spiral configuration. The device includes a plurality of linear electrodes, 552, 554, aligned perpendicularly to the channel cross sections. If the sweat sample completely fills the channel, the excess sweat will then be transported into a sweat collection reservoir or pump 560, or passed out of the device at a drain (not shown). The channel 530 will have determined volumes in between the points where an electrode intersects the channel cross-section. In this embodiment, a sweat sample 14 enters the microfluidic channel 530 at the inlet 532, and flows along the channel, where it contacts the first electrode 552. With continued active sweating, the sweat sample then fills the channel until it contacts the second electrode 554, completing a detection circuit 556 and causing the device to register a current flow. Similarly to the previous embodiment, as the sweat sample continues to fill the channel and establishes a second contact between the electrodes, the device will register an increase in current through the circuit. In other embodiments (not shown), the channel may include individual electrodes, as depicted in the FIG. 2 embodiment, or may have other suitable electrode arrangements capable of providing a detection circuit for sweat rate determination.

Some embodiments of the disclosed invention employ advanced techniques known in the art of microfluidics to manipulate the flow resistance of a sweat sample moving through a device. See Safavieh, R., et al., "Serpentine and leading edge capillary pumps for microfluidic capillary systems," *Microfluid Nanofluid*, (2015) 18: 357-366. Traditional channel designs can present drawbacks for sweat sensing applications. For example, longer channels may impose hydraulic resistance against the movement of sweat into the channel, especially as the channel becomes filled, and the mass of fluid in the channel tends to resist further movement. Similarly, high sweat rates may cause sweat in parts of the channel to move more rapidly, which results in additional flow resistance due to changing contact angles between the sweat and the channel surface. In addition, due to uneven filling of the channel at the filling front, i.e., the leading edge of the sweat sample, bubbles can form within the channel. These factors will tend to cause uneven flow through the channel, or leakage of sweat out of the channel, both of which diminish device accuracy.

Figure 6:
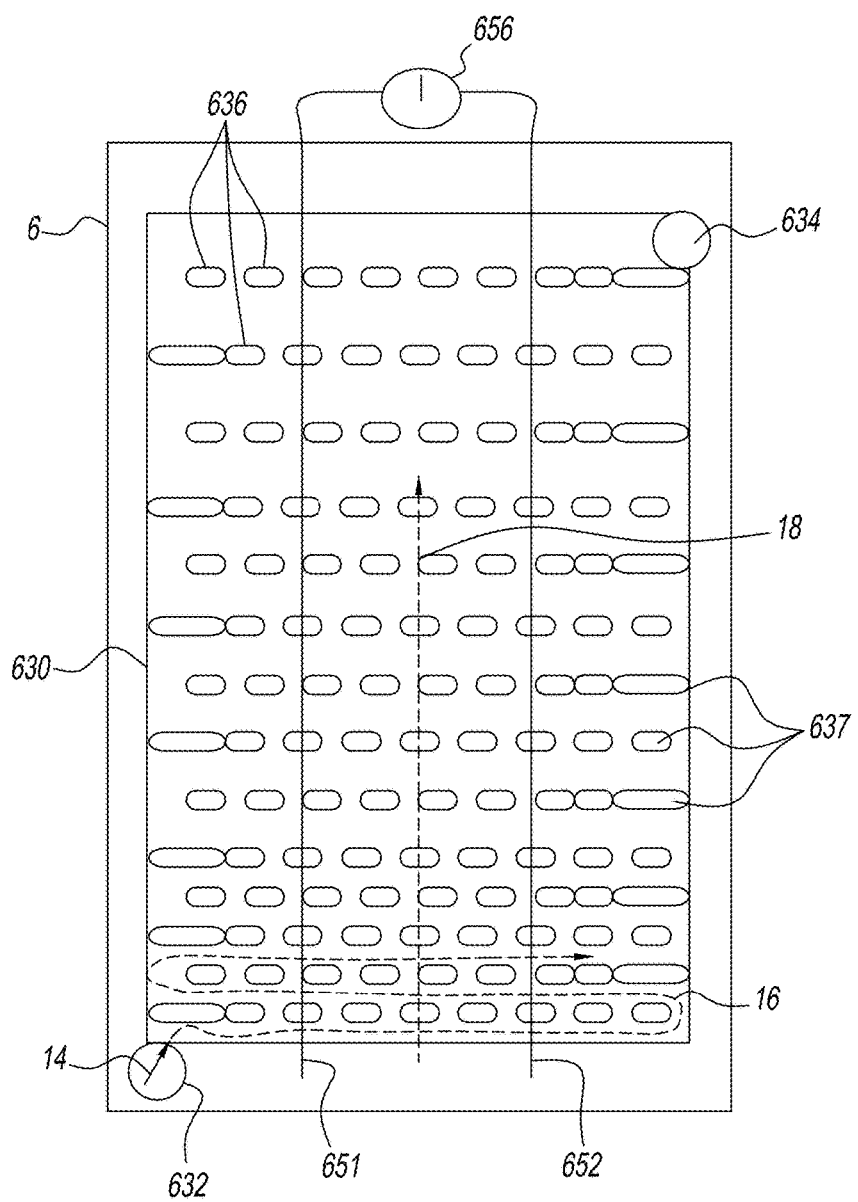
FIG. 6 represents at least a portion of an embodiment of the disclosed invention configured to measure volumetric sweat rate.
Figure 6A:
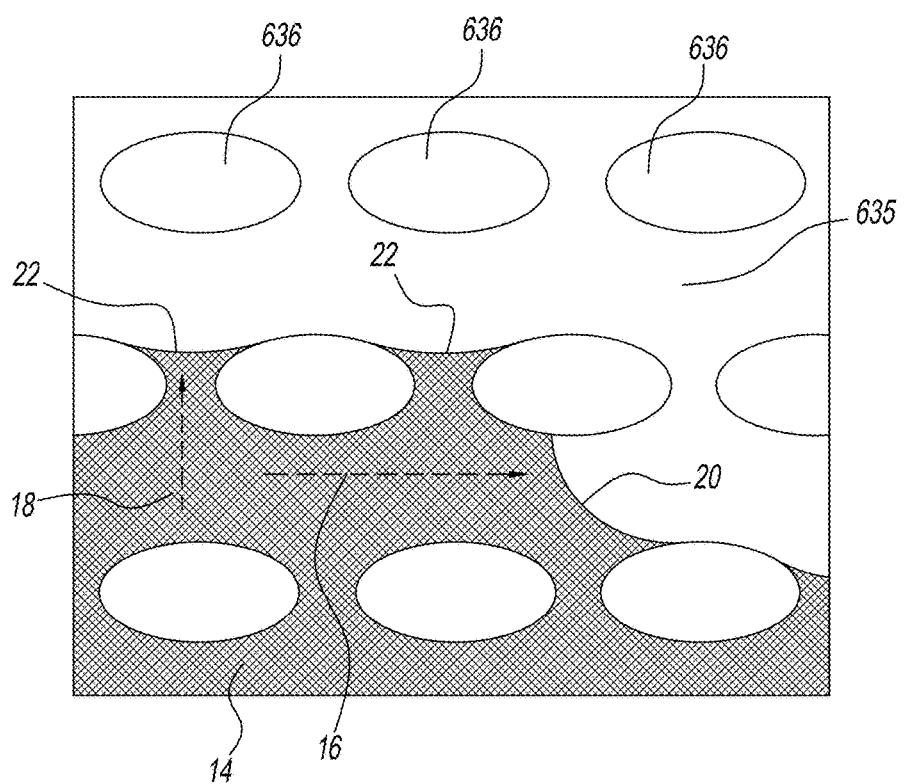
FIGS. 6A and 6B represent close-up views of at least a portion of the device depicted in FIG. 6.

With reference to FIG. 6, therefore, an embodiment of the disclosed invention includes a microfluidic capillary pump to facilitate and manage sweat flow through the device. A sweat sample 14 enters the device through an inlet 632, and moves into the capillary pump 630. The capillary pump 630 is comprised of a hydrophilic channel 635 that is defined by a plurality of hydrophilic oval microposts 636, arranged in rows 637, with the posts in each subsequent row staggered laterally with respect to the previous row. Examples of suitable hydrophilic materials for use in the channel and microposts include silicon dioxide, titanium dioxide, aluminum dioxide, hydrogels, and polymers, such as poly(2-hydroxyethyl methacrylate), sulfonated polyesters, and polymer salts. The capillary pump guides the sweat along each section of the channel (depicted in the present embodiment as a serpentine channel, but not so limited) by the geometry of the microposts, providing a determined filling front for the sweat sample. With reference to FIG. 6A, depicting a close-up view of the microposts, as sweat 14 moves through the capillary pump, the filling front 20 fills along the channel in the direction of the arrow 16. Sweat wets in between microposts 18, but is unable to flow between the microposts due to a temporary capillary stop valve 22, created by the negative pressure of the filling front 20 in the channel. Once an entire channel section is filled across, sweat can then flow in between the microposts, reducing overall flow resistance in a predictable and controlled manner.

With further reference to FIG. 6, the filling front thus moves in a serpentine path along the direction of the arrow 16, while the main mass of sweat flow moves along behind the filling front in the direction of the arrow 18. Flow resistance along the channel can be adjusted by spacing the rows further apart or closer together. As depicted, the channel becomes wider as it moves along toward the outlet 634, thus producing lower flow resistance. By such techniques, sweat sample flow can be managed to achieve accurate measurements of sweat rate. The sweat rate detection electrodes and circuit for the capillary pump configuration may be configured similarly to other embodiments herein. For example, the device may include a first electrode 651 and a second electrode 652 that form part of a detection circuit 656. As the filling front moves along the channel, the detection circuit 656 will detect an increasing current as more sweat fills the device. In other embodiments (not shown), the channels may include individual electrodes, as depicted in the FIG. 2 embodiment, or may have other suitable electrode arrangements capable of providing a detection circuit for sweat rate determination.

Figure 6B:
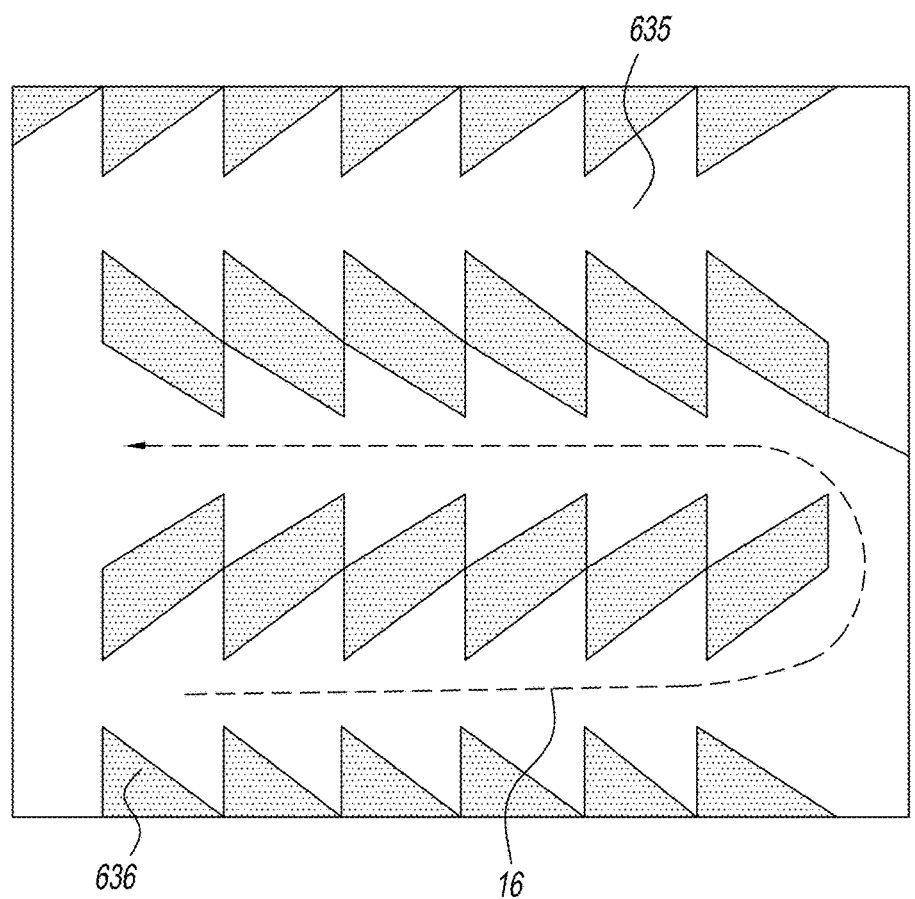
Figure 7:
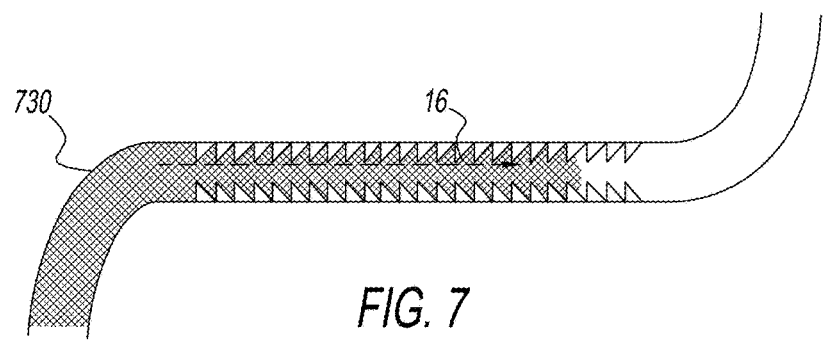
FIGS. 7, 7A and 7B represent close-up views of at least a portion of the device depicted in FIG. 5.

With reference to FIG. 6B, another embodiment of the device depicted in FIG. 6 includes a channel 635B having a directional flow geometry. As is known by practitioners skilled in the art of microfluidics, various configurations are possible that use fluid contact angles with the channel surfaces to produce a lower resistance to fluid flow in the direction of the arrow 18, while providing higher resistance to flow in the opposite direction. This arrangement can also be used with the capillary pump configuration, in which the hydrophilic posts, rather than having an oval shape, would be shaped and oriented to create contact angles promoting forward fluid movement, while also allowing mass fluid movement to occur between posts behind the filling front. Directional geometry can be used with other embodiments of the disclosed invention to improve fluid movement through the device, for example FIG. 7 depicts a serpentine channel of the device in FIG. 5 that includes directional flow geometry.

Figure 7A:
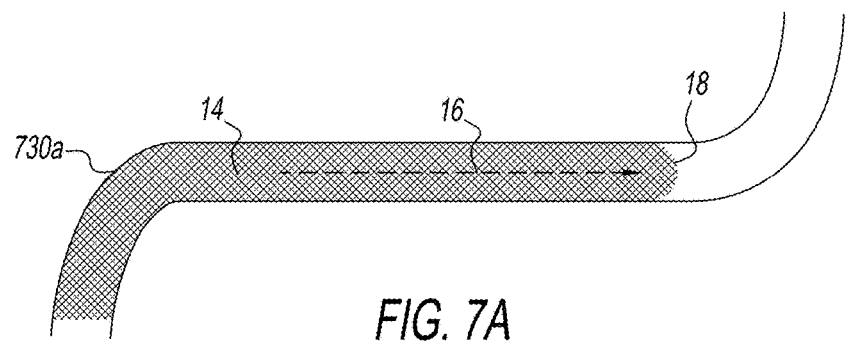
Figure 7B:
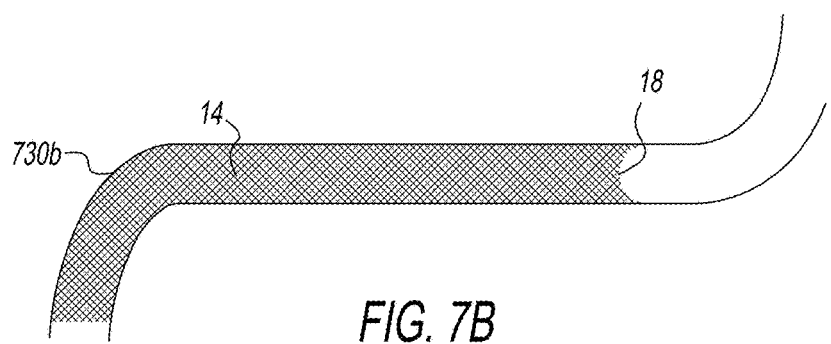

With reference to FIG. 7A, in other embodiments, rather than include directional flow geometry, a microfluidic channel 730A may simply include a hydrophobic coating that tends to resist movement of the sweat sample 14 in either direction. The channel coating would be formulated to create a contact angle hysteresis of greater than 30 degrees between the sweat sample and the channel. Thus, when the device wearer is actively sweating, positive pressure from the sweat gland will tend to move the sweat sample forward in the direction of the arrow 16 despite resistance from the channel. However, as depicted in FIG. 7B, when active sweating stops, or if there is any other flow interruption, the channel coating's resistance to movement in either direction will tend to keep the sweat sample stationary. Therefore, interruptions in flow will not cause sweat to slosh forward or backward in the channel.

Figure 8:
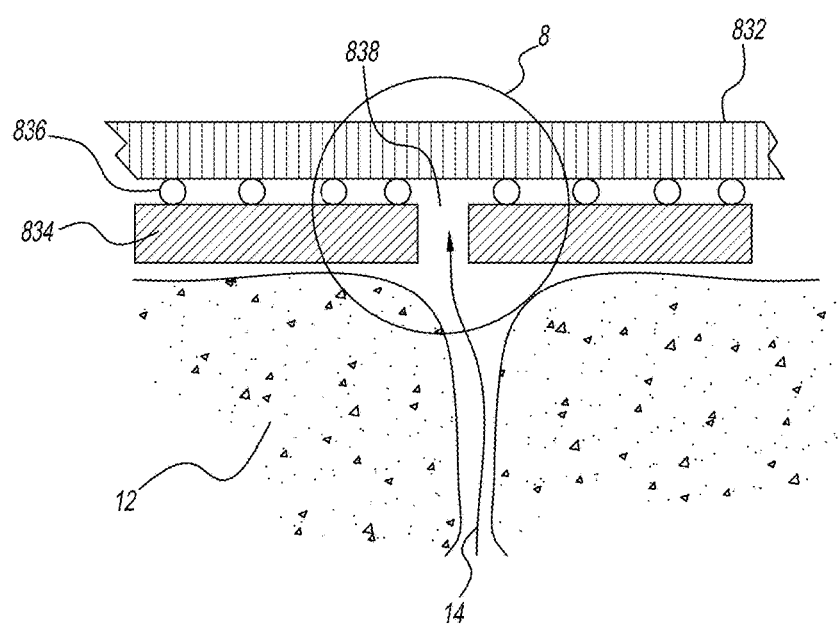
FIGS. 8 and 8A depict at least a portion of an embodiment of the disclosed invention where the inlet includes an interruptible capillary interface.
Figure 8A:
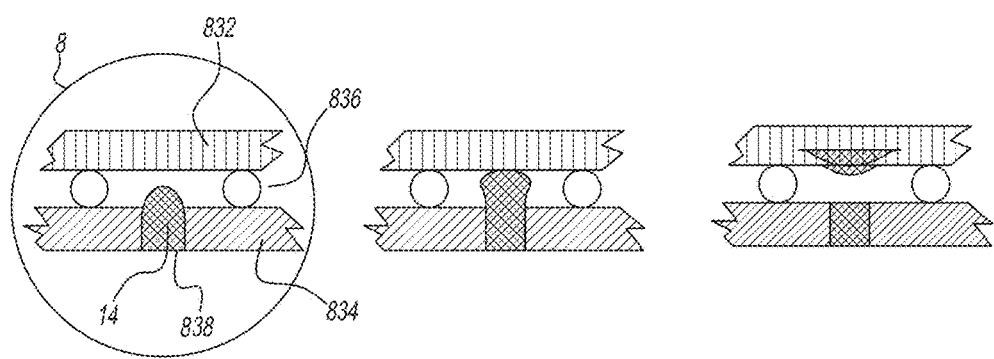

With reference to FIG. 8, embodiments of the disclosed invention may benefit from having an interruptible capillary configuration between the skin 12 and the device inlet or channel 832. Because some embodiments of the device rely on positive pressure from the skin to drive a sweat sample into the inlet or channel, if the device is subsequently pulled away from the skin, suction may be created that will tend to pull the sweat sample back out of the device. Therefore, to minimize this reverse or variable flow, the device may be fitted with an interruptible capillary interface. A polymer layer 834, e.g., PET, PEN, PTFE, polyimides, nafion, or semipermeable membranes, is placed between the skin 12 and the channel 832, and is separated from the channel by a plurality of spacers 836. In such embodiments, the collection channel or wick must be capable of exerting negative pressure on the sweat sample to help draw the sample through the device. The polymer layer 834 has a plurality of openings or pores 838 that allow sweat to pass from the skin 12 to the channel 832 by means of positive pressure from sweat generation by the skin. FIG. 8A depicts a close-up of the area within the circle 8. As sweat is generated by the skin, positive pressure forces the sweat through the pore 838, where it contacts, and then is wicked into, the channel 832. The capillary action is discontinuous, meaning that sweat will push into contact with the inlet only when there is sufficient positive pressure from the skin. This allows the device to collect a sweat sample without creating a vacuum that would pull sweat back out of the device when the device is moved relative to the skin's surface.

Figure 9:
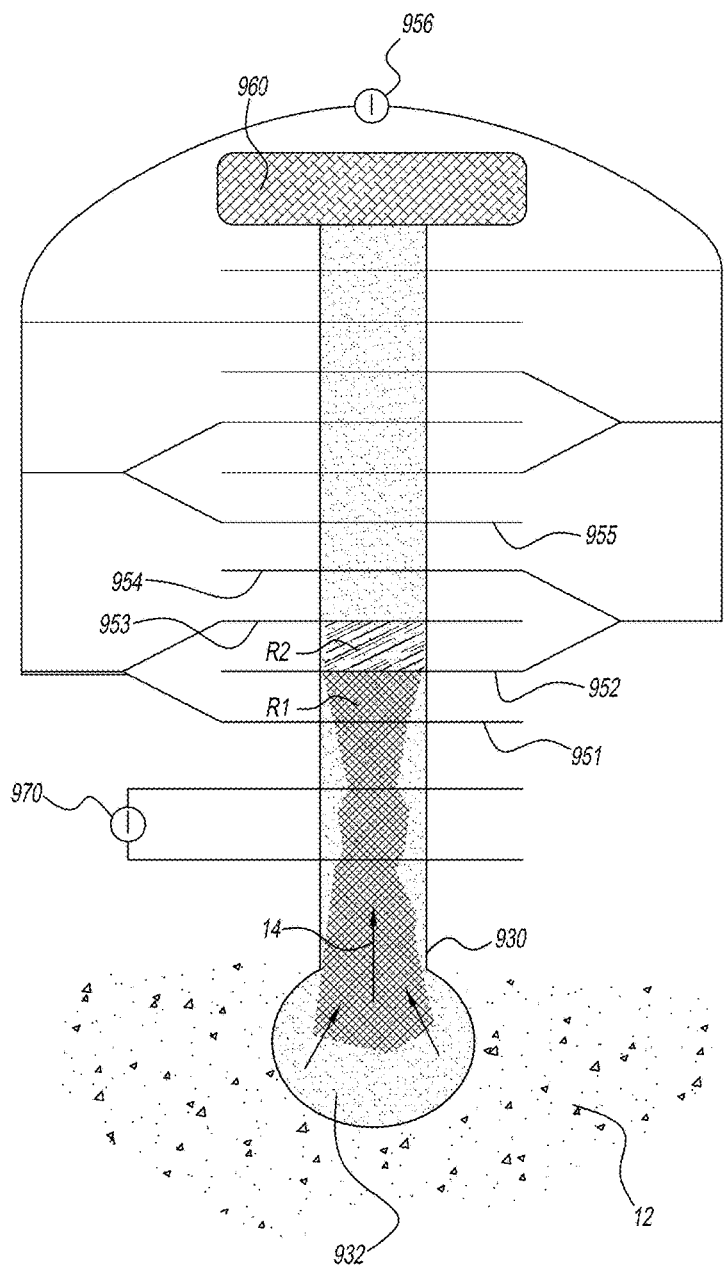
FIG. 9 depicts at least a portion of an embodiment of the disclosed invention configured to measure sweat conductivity and to volumetrically determine sweat sample flow rate.

With reference to FIG. 9, another embodiment of the disclosed invention includes a sweat sample collector 930. The device also includes a plurality of interdigitated electrodes 951, 952, 953, 954, 955, that cross the sample collector 930 at set intervals with the interspersed collector sections having determined volumes. Materials for the sample collector may include, without limitation, rayon, polymers, composite materials, membranes, coated or textured materials, textiles, microfluidics, or other suitable materials having the ability to absorb sweat, but exerting little or no wicking pressure on the sweat sample. Materials capable of providing suitable characteristics are well-known by those skilled in the art of materials science and microfluidics. If the sweat sample completely fills the sample collector, excess sweat will then be transported into a sweat collection reservoir or pump 960, or passed out of the device at a drain (not shown). In some embodiments, the sample collector may instead incorporate a microfluidic channel as discussed for previous embodiments. When sweat is generated and collected from the skin 12 by the sample collector 930, the sweat sample 14 enters the collector, and active sweating will push sweat across the electrodes 951, 952, 953, 954, 955. When sweat contacts the first electrode 951, and then contacts the second electrode 952, the detection circuit 956 will be completed, and the device will register current across the circuit. As with previous embodiments, as sweat continues to move into contact with additional electrodes, additional collector sections filled with sweat will act as parallel resistors in the circuit 956. Thus, as sweat continues to fill each determined collector volume between electrodes, the device will register the time required to fill that volume as an increase in current across the circuit 956. The device then translates this volume per time period measurement into a sweat rate.

Some embodiments may include an optional sweat conductivity circuit 970 located near the collection area 932. The sweat conductivity circuit 970 would include a plurality of conductivity electrodes 972, 974 that intersect the sample collector 930 so that any collected sweat will contact the electrodes. In use, sweat is generated by the skin 12 and collected by the sample collector 930. When sweat contacts at least two conductivity electrodes 972, 974, the circuit will be completed, and the device will detect a voltage across the conductivity circuit. Described in more detail below, the device will interpret this voltage as an indication of the conductivity of new sweat as it is generated and collected by the sample collector.

The volumetric sweat rate sensor as described herein does not report sweat rate in real time, but instead reports an average rate at which the sweat sample fills the channel volume between switches. During periods of constant or increasing sweat rate, the device will provide the most accurate "real-time" sweat rate information, since sweat will fill the subsequent (same volume) channel section and activate the next switch after the same or a shorter time than for the previous switch. However, during periods of decreasing or zero sweat rate, reported sweat rates will be less accurate. This is because during slowed sweating, the sample will take longer to reach the next switch, but the sensor will not detect when, or by how much, the sweat rate slowed during the sample's movement between switches. Thus, techniques to improve the reported sweat rate during such periods will be beneficial.

One means of improving the real-time reported sweat rate value during periods of decreasing sweat rate includes the use of prospective and retrospective sweat rate estimates. The volumetric sensor constructs a sweat rate based on the time required for the sweat sample to fill the channel volume between switch A and switch B, or $$r_{AB} = \frac{V_{AB}}{t_{AB}}.$$

While sweat fills the channel volume between switch B and switch C, the sensor continues to report the last sweat rate value $r_{AB}$ as the prospective sweat rate estimate until the sweat contacts switch C, or until an estimated fill time is reached. The estimated fill time is the expected time required to fill the B to C channel volume at the previous sweat rate. If the estimated fill time lapses before C is contacted, a retrospective estimate will be calculated by factoring the additional time into the rate. Once the sweat sample reaches switch C, the B to C sweat rate is calculated by dividing the B to C channel volume by the elapsed time since the sweat sample contacted switch B.

For example, if the A to B channel volume is 1 μL, and the A to B fill time is 5 minutes, the calculated sweat rate would be 200 nL/min. If the B to C channel volume is 1.5 μL, the estimated fill time will be $$t_{BC} \approx \frac{V_{BC}}{r_{AB}},$$

or 7.5 min. While sweat fills from B to C, the prospective sweat rate estimate will be 200 nL/min until the 7.5 minute point is reached, then the retrospective rate estimate will be reported. The retrospective estimate becomes $$r_{BC} \approx \frac{V_{BC}}{t_e},$$

where $t_e$ is the time elapsed since sweat contacted switch B, e.g., $t_e$=7.7 minutes, or $$r_{BC} \approx \frac{1.5 \; \mu L}{7.7} \approx 195 \; nL/min.$$

Once C is contacted, at $t_{BC}$=8 min, the B to C sweat rate is recalculated as $$r_{BC} = \frac{1.5 \; \mu L}{8 \; min} = 188 \; nL/min.$$

Figure 10:
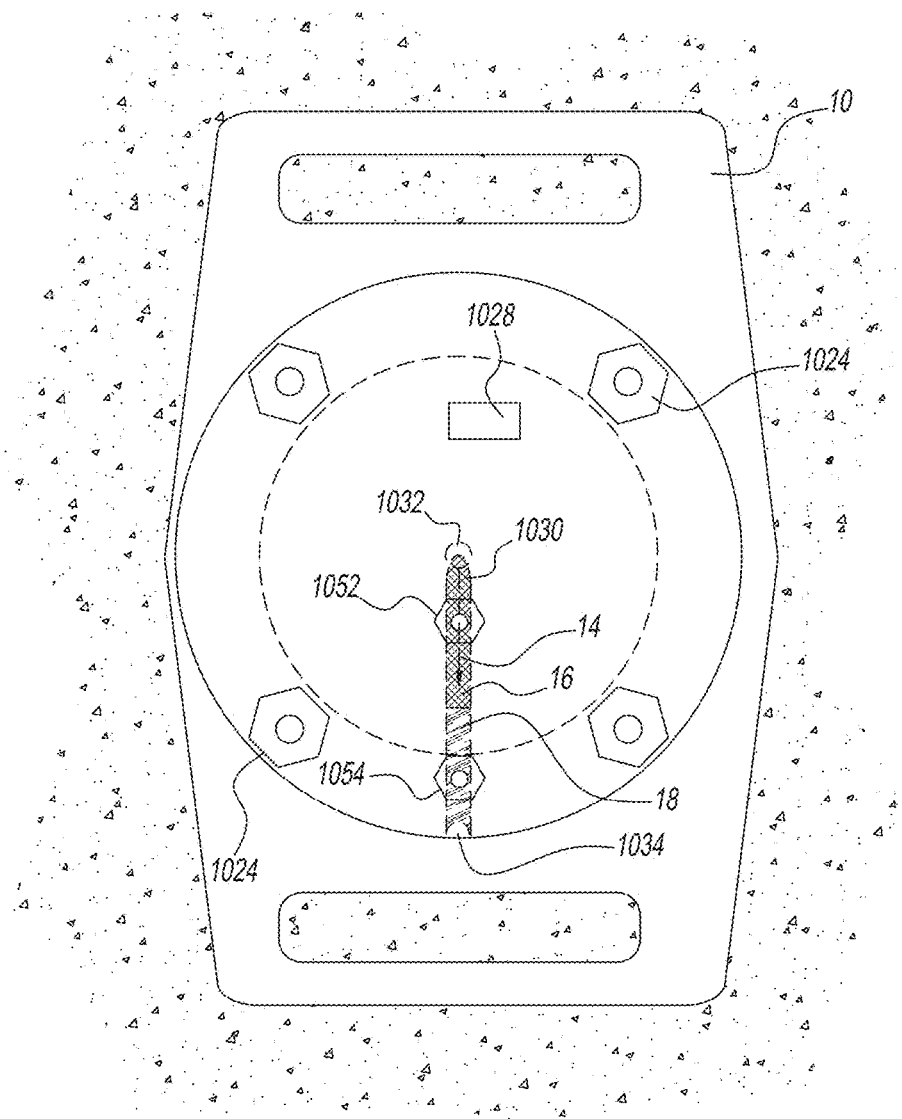
FIG. 10 represents at least a portion of an embodiment of the disclosed invention configured to measure sweat conductivity and GSR.

In addition to the above device and method for volumetric sweat rate measurement, estimation, and reporting, the disclosed invention also includes devices and methods for measuring sweat conductivity contemporaneously with galvanic skin response. With reference to FIG. 10, a sweat sensing device 10 including a sweat conductivity sensor and GSR sensor(s) 1024, is placed on skin 12, and configured to determine sweat rate, seat onset, sweat cessation, and sweat ion concentrations. The sweat conductivity sensor includes a microfluidic channel 1030, a plurality of electrodes 1052, 1054 placed in fluidic contact with the channel (two are shown), and a temperature sensor 1028. In some embodiments, the temperature sensor is combined with a GSR electrode (not shown). During device operation, when the wearer begins to sweat, a sweat sample 14 will move into the device at an inlet 1032 and through the microfluidic channel 1030. The electrodes 1052, 1054 will measure the conductivity of the sweat sample, which will be processed by the device, and transformed into a sweat rate or sweat ion concentration value. The sweat sample will then be wicked into a sweat collection reservoir (not shown), or passed out of the device at a drain 1034. During active sweating, sweat leaves the sweat gland, enters the channel 1030, and collects in a sweat volume between electrodes 1052, 1054. When the sweat volume is initially filled, and a conductivity measurement taken, the sweat sample is regarded as consisting entirely of new sweat. As new sweat 16 continues to enter the channel, but before the older sweat 18 exits the device via the drain 1034, and is displaced by new sweat 16, the sweat sample will consist of a mix of older sweat and newer sweat.

Sweat conductivity measurements can be used to estimate sweat rate because sweat conductivity is heavily dependent on sweat's $Cl^-$ content, which represents the vast majority of negative ions in sweat, and because sweat $Na^+$ and $Cl^-$ concentrations are correlated with sweat rate, as evidenced by various studies in the relevant literature. See, e.g., Sato, K., et al., "Biology of sweat glands and their disorders," *J. of the Am. Academy of Dermatology*, p. 552 figure 2, 20/4/April 1989. Sodium and $Cl^-$ enter sweat in the secretory coil of the eccrine sweat gland, and at negligible sweat rates, are isotonic with interstitial fluid concentrations of $Na^+$ and $Cl^-$. Bovell, *Journal of Local and Global Health Science*, p. 9, 2015:5. With the initiation of sweating, $Cl^-$ is pumped into the lumen of the gland, where its negative electrical potential pulls in $Na^+$. The $Na^+$ and $Cl^-$ combine to form NaCl, which creates an osmotic gradient that draws water into the lumen. As the newly created sweat moves out of the secretory coil, $Na^+$, with $Cl^-$ in tow, is reabsorbed through the duct and re-enters the interstitial fluid.

Figure 11:
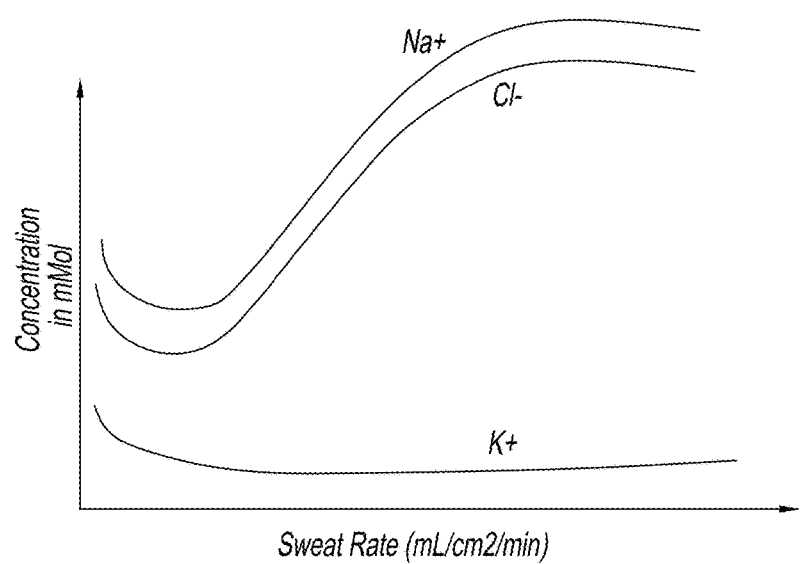
FIG. 11 is a graphic depiction of sweat ion concentrations as they relate to increases in sweat rate.

With reference to FIG. 11, at lower sweat rates, 0.0 to 0.4 $\mu L/cm^2/min$, relatively more of the $Na^+$ and $Cl^-$ are reabsorbed by the sweat duct so that sweat reaching the skin has lower concentrations of $Na^+$ and $Cl^-$. Amano, T., et al., "Determination of the maximum rate of eccrine sweat glands' ion readsorption using galvanic skin conductance to local sweat rate relationship," *Eur. J. Appl. Physiology*, p. 4, DOI 10.1007/s00421-015-3275-9. Initially, between 0.2 and 0.4 $\mu L/cm^2/min$ sweat rate, the $Na^+$ gland reabsorption rate is at is maximum (around 85%), which translates to sweat $Na^+$ concentration of 10-15 mMol. Sato, K., et al., "Biology of sweat glands and their disorders," *J. of the Am. Academy of Dermatology*, p. 552, 20/4/April 1989, p. 552; Buono, M., et al., "$Na^+$ secretion rate increases proportionally more than the $Na^+$ reabsorption rate with increases in sweat rate," *J. Appl. Physiology*, 105:1044-1048, 2008. As sweat rate increases, the amount and speed of $Na^+$ flowing through the duct overwhelms the reabsorption mechanism, so that at sweat rates above 0.4 $\mu L/cm^2/min$, the duct absorbs a significantly lower percentage of $Na^+$, down to about 65% of $Na^+$ at a sweat rate of 0.8 $\mu L/cm^2/min$. Buono, M., et al. As a result, $Na^+$ concentrations show a linear increase with increases in sweat rate in the range of about 20 mEq/L for a 0.4 $\mu L/cm^2/min$ sweat rate, to 60 mEq/L for a 1.5 $\mu L/cm^2/min$ sweat rate. Allen, J., et al., "Influence of acclimatization on sweat sodium concentration," *J. of Applied Physiology*, 30/5/May 1971, at 710; Bovell, at 11; see also, Buono, at 1025. (0.25 $\mu L/cm^2/min$ sweat rate correlated to 20 mMol/L Nat, 0.9 $\mu L/cm^2/min$ sweat rate correlated to 55 mMol/L $Na^+$). For individuals that acclimatize to warmer environments, or who engage in physical conditioning, the body's ability to reabsorb $Na^+$ improves, and sweat profiles for these individuals will tend to have sweat $Na^+$ concentrations about 15 mMol lower than for unconditioned individuals. Allen, J., et al., at 710. Chloride concentrations roughly correspond to $Na^+$ levels for various sweat rates, due to the abundance of NaCl in sweat. These results for $Na^+$ and $Cl^-$ concentrations as they correlate to sweat rate are less certain at low sweat rates, i.e. below 0.4 $\mu L/cm^2/min$, where the $Na^+$ production is not yet overwhelming the duct's ability to reabsorb $Na^+$.

As discussed above, since $Cl^-$ (and $Na^+$) concentrations exhibit a linear relationship with sweat rates, higher conductivity values therefore reflect higher sweat rates. See Liu, G., et al., "Real-time sweat analysis via alternating current conductivity of artificial and human sweat," *Applied Physics Letters*, 106, 133702 (2015); doi: 10.1063/1.4916831, figure 2. Once the device correlates the measured sweat conductivity with a $Cl^-$ concentration, it could then use a lookup table or other suitable method, such as the use of an empirically-derived database, to estimate sweat rate. Fundamentally, however, sweat conductivity alone is an imperfect proxy for sweat rate, since it is unable to distinguish between a change in sweat ion concentration and a change in sweat rate. Sweat conductivity, for example, could not identify when an increased conductivity reading is due to increased sweat $Cl^-$ concentration that occurred during a period of stable or decreasing sweat rate. In addition to this fundamental limitation, sweat conductivity is also subject to significant sensor-to-sensor, individual-to-individual, and day-to-day variabilities. Further, the sweat conductivity sensor as described herein will have an inherent time lag based on the time required to fill the sweat volume with new sweat. The time required to fully refresh the sweat volume with new sweat is the sample refresh time, and is inversely proportional to a chronologically assured sweat sampling rate (i.e., a sampling rate that measures analyte concentrations when the sweat volume is fully refreshed with new sweat). If the sweat conductivity sensor takes measurements at a sampling rate that is faster than the chronologically assured sampling rate, the conductivity measurement will not reflect new sweat concentration, but rather an average of the new and old sweat concentration. Therefore, sweat conductivity-based sweat rate and ion content estimates would be improved by performing calibration or adjustment to account for such factors, for example as disclosed herein, by incorporating contemporaneous volumetric sweat rate and GSR measurements.

Figure 12:
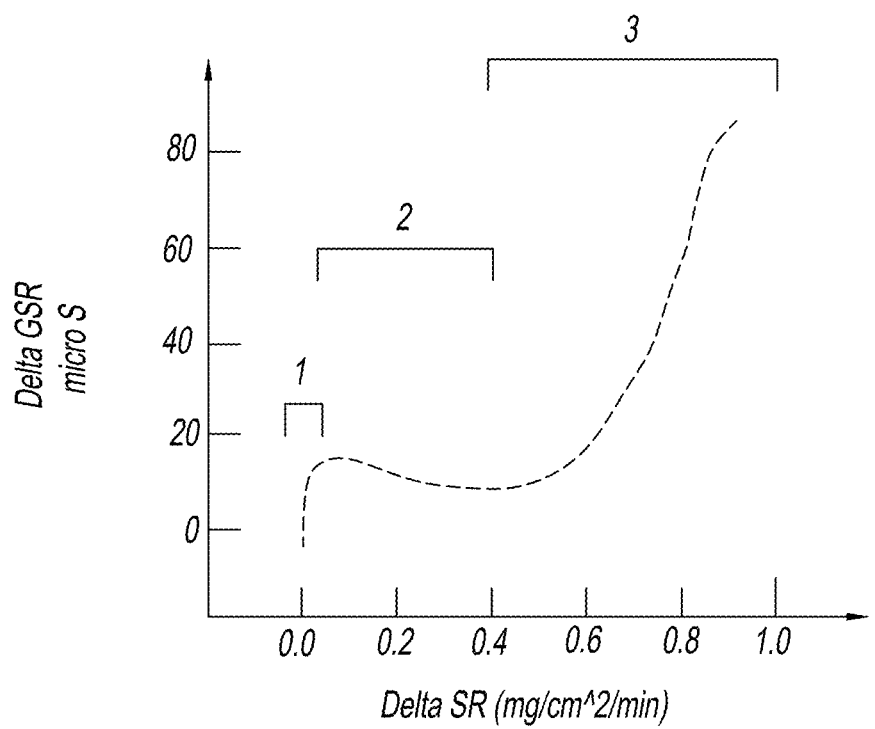
FIG. 12 is a graphic depiction of change in GSR as it relates to change in sweat rate.

Like sweat conductivity, GSR readings reflect a profile associated with sweat concentrations of $Na^+$ and $Cl^-$, and can therefore be used to approximate sweat rate. See Amano, T., et al. Skin conductivity as measured by GSR sensors is dominated by the component attributable to the sweat glands, and within the sweat glands, the dominant component is sweat and its most abundant ions, $Na^+$ and $Cl^-$. With reference to FIG. 12, GSR measurements indicate three phases: (1) a pre-sweating period, in which GSR increases while sweat rate remains negligible (representing the sweat duct filling with sweat); (2) a low sweat rate phase, corresponding to sweat rates below 0.4 $\mu L/cm^2/min$, during which sweat rate increases while GSR stays roughly constant; and (3) a linear phase above 0.4 $\mu L/cm^2/min$ in which the sweat rate increases linearly with GSR. See Amano, T., et al. Unlike sweat conductivity, however, GSR does not suffer significant lag time between changed sweating conditions and changed electrical signal output. Therefore, GSR can serve as a practically instantaneous measure of sweat onset or cessation.

Also like sweat conductivity, GSR suffers from a fundamental limitation as a standalone proxy for sweat rate or sweat ion concentration, since GSR is a composite measurement that includes a sweat rate component, a sweat ion (conductivity) component, and a skin contact resistance component. Consequently, GSR readings alone cannot distinguish among these components when attributing cause to a change in GSR value. For example, GSR may register an increase due to a dilation of the sweat duct, which would be indistinguishable from a sweat rate increase. Additionally, compared to sweat conductivity, GSR readings show even more variability across individuals and across uses by an individual, largely due to the contribution of skin contact resistance. Accordingly, GSR's value as a proxy for sweat rate or sweat ion concentrations would also be improved by incorporating contemporaneous sweat conductivity and volumetric sweat rate measurements. For example, sweat conductivity measurements can be used to isolate the contribution made to GSR by skin contact resistance, while volumetric sweat rate can be used to isolate the contribution made to GSR by ion concentration.

Figure 13:
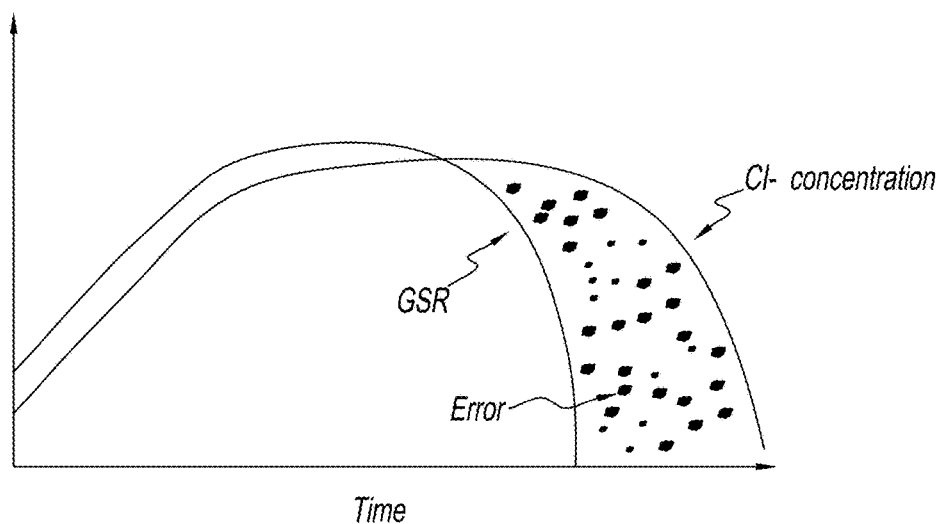
FIG. 13 is a graphic depiction of change over time of GSR and Cl⁻ concentration (or sweat conductivity) through a sweating cycle.

To illustrate how sweat conductivity and GSR measurements can be used to complement each other, the following example is offered. With further reference to FIG. 10, as a sweat sample enters the channel 1030, and initially fills the channel volume between electrodes 1052, 1054, a first sweat conductivity reading is taken. GSR readings are taken during the time required to fill the channel volume and contemporaneously with the first conductivity measurement. Subsequently, as new sweat 16 enters the channel, but before the older sweat 18 has completely exited the device, sweat conductivity measurements will not reflect the conductivity of new sweat, and will lag the GSR measurements. While sweat rate is increasing or if sweat rates are high, mixing of old and new sweat will be more rapid, allowing conductivity measurements to track actual sweat conductivity and GSR measurements more closely. Once sweat rate begins to decrease, however, GSR will quickly reflect lower skin/sweat gland conductivity, while sweat conductivity measurements will remain elevated. Such a sweat conductivity/GSR split is depicted in FIG. 13, in which a sweating begins, increases through the linear regime, and then declines. GSR change measurements track with sweat conductivity measurements during the portion of the cycle where sweat rate is increasing, but lead sweat conductivity while sweat rate is decreasing. If a sweat sensing device were to continue to sample sweat conductivity at rates above the chronologically assured sampling rate, and then calculate sweat rate and ion concentrations based on these lagging conductivity measurements, many sweat sensing device functions would suffer in accuracy. For example, estimates of total water loss or electrolyte loss can be significantly overestimated, especially for sweat sensing applications where the wearer experiences multiple sweating cycles. However, if GSR measurements are used to correct sweat conductivity, greater accuracy can be achieved.

During device operation, therefore, if GSR and conductivity readings indicate the initiation of a sweat cycle, a subsequent GSR change indicating a decrease in skin conductivity is used to indicate the timing of sweat rate decrease. The GSR change during this portion of the sweat cycle may then used to approximate sweat rate and sweat ion concentration. The device can also use GSR change to slow sweat sampling rates to improve chronological assurance. Lagging sweat conductivity measurements can also be discarded or corrected to account for the decreasing sweat rate.

A sweat sensing device can also be configured to correct conductivity readings during the declining portion of a sweat cycle by modeling how the mixing of old and new sweat affects sweat conductivity readings. With such a model, the device may more accurately interpret its measurements to reflect new sweat conductivity. As a first-order correction, the device may model the sweat sample as a fixed volume with new sweat added and old sweat displaced. Each volume of new sweat displaces an equal volume of old sweat from the sweat sample. The model also assumes instant mixing of new sweat with old sweat in each time period dt. With a known sweat volume and accurate sweat rate measurement that is independent of sweat conductivity, e.g., GSR measurements, the model can accurately calculate the area under the conductivity curve that is due to old sweat, which may then be subtracted from the conductivity readings to provide the new sweat conductivity value during periods with decreasing sweat rates. Some embodiments use micro-thermal flow sensors, ISE measurements, or other suitable measurements to supply the independent sweat rate. The model may also be improved by including a mixing function that would account for the sweat volume's physical geometry, sweat rate and or wicking rate.

In other embodiments, sweat conductivity and GSR readings can be used in conjunction with contemporaneous ISE-derived sweat ion measurements to provide improved calculations of sweat rate and ion concentrations. Comparisons of GSR/sweat conductivity and measurements of ISEs may need to be adjusted to account for sensor response lag by the ISEs to ensure truly contemporaneous measurements are being compared. In addition, because GSR shows broad individual variability, correlating GSR with sweat $Na^+$ or $Cl^-$ concentrations would benefit from some form of calibration. For example, when a sweat sensing device is first activated and taking measurements on a wearer, the device may compare sweat conductivity and GSR changes throughout the three GSR sweating regimes. The device could then correlate Cl⁻ concentrations to sweat conductivity readings for each regime, and by extension, a calculated sweat rate. Then, during subsequent sweating cycles, the device could measure sweat conductivity change and calculate a sweat rate based on the Cl⁻ value correlated to that conductivity measurement in the appropriate sweat regime. In other embodiments, calibration of sweat conductivity to Cl⁻ concentration could be accomplished beforehand by aggregating data for a particular individual, a particular phenotype, a fitness level, an age range, or other relevant characteristic. The correlated aggregated data may then inform a subsequent use of a sweat sensing device to improve sweat rate calculations for a wearer.

Because each of volumetric sweat rate, GSR, and sweat conductivity makes important contributions to the physiological picture, a preferred application is to combine contemporaneous measurements from each of these sensor types to create composite sweat rate and sweat ion concentration estimates. Therefore, a preferred embodiment of the disclosed invention combines volumetric sweat rate measurements with sweat conductivity measurements and GSR measurements to inform sweat rate, and to provide sweat ionic content, sweat onset and sweat cessation information. Accordingly, with reference to FIG. 14, a sweat sensing device 140 of the disclosed invention, including a volumetric sweat rate sensor, a sweat conductivity sensor, and a GSR sensor, is placed on a wearer's skin 12. The device includes a concave sweat collection area 1436 that moves sweat from skin into an inlet 1432, which is in fluidic communication with a microfluidic channel 1430 that terminates in an outlet 1434 or sweat collection reservoir (not shown). The sweat conductivity sensor includes at least one set of electrodes 1420 placed upon a substrate (not shown), such as a printed circuit board, and arranged across the channel 1430, preferentially near the inlet 1432. The GSR sensor includes a plurality of electrodes 1424 (four are shown) arranged on the device so that the electrodes are spaced approximately 1 to 3 cm apart, and contact the wearer's skin outside the collection area 1436. The volumetric sweat rate sensor includes a plurality of electrodes 1454 which are also carried on the substrate and arranged across the channel 1430. As described for FIG. 3, the electrodes are spaced at intervals with known intervening channel volumes. During device operation, when the wearer begins to sweat, a sweat sample 16 will enter the device at the inlet 1432 and move through the channel 1430. As sweat flows through and contacts the conductivity electrode 1420, the device measures the conductivity of the sweat sample. Similarly, as sweat moves further into the channel, it flows through and contacts the volumetric sweat rate electrodes 1426 in succession, which the device interprets as sweat being present at the contacted electrode. The device uses sweat's presence at each electrode, along with the intervening filled channel volume and the time of contact to determine volumetric sweat rate. In some embodiments, each sweat volume electrode 1426 is also configured to measure sweat conductivity as sweat contacts it. Some embodiments of the device may include a micro-thermal mass flow sensor, a pressure-based sensor, or other suitable means to independently determine sweat rate. Other embodiments may include a temperature sensor 1428, or a temperature sensor can be incorporated into one of the GSR electrodes (not shown). Some embodiments are configured with a disposable microfluidic channel 1430 (not shown). While other embodiments include a reusable microfluidic channel that is cleaned in between uses, for example by removing the channel 1430 from the device and flushing it with air, deionized water, or a cleaning solution, or having components that can be separated and cleaned (not shown). Additionally, an embodiment can use additional microfluidic components as necessary to control flow of the sweat sample, e.g., valves, and wicking components. Some embodiments may also include sensors, such as ISEs or amperometric sensors to measure other ions contributing to conductivity, such as K⁺, lactate and urea.

Figure 14:
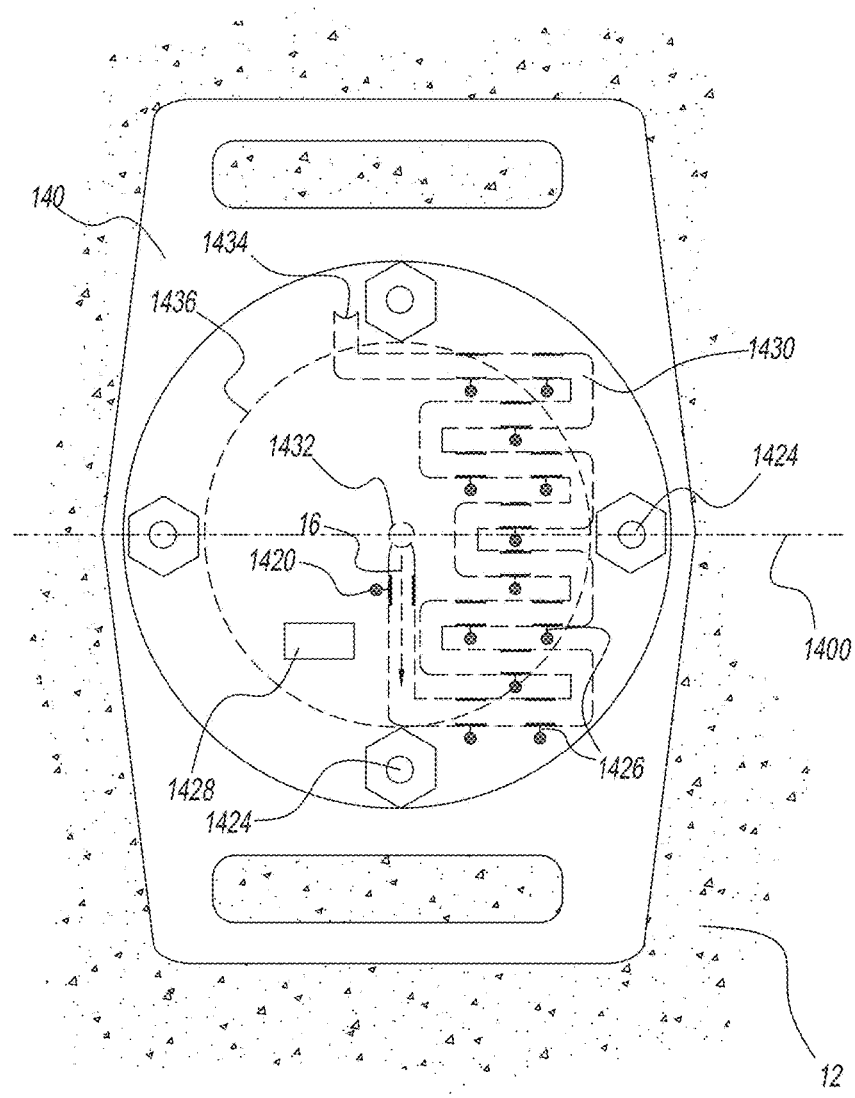
FIG. 14 represents at least a portion of an embodiment of the disclosed invention configured to measure sweat conductivity, GSR, and volumetric sweat rate.
Figure 14A:
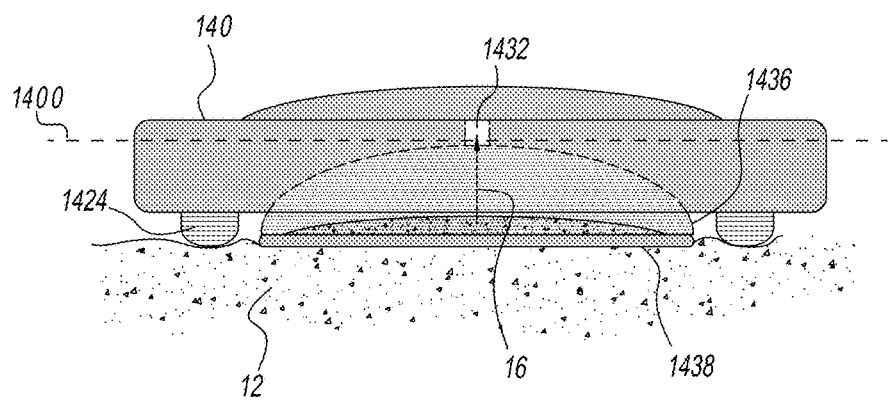
FIG. 14A is a cross sectional side profile view of the device depicted in FIG. 14.

With reference to FIG. 14A, a side profile view of a device of the disclosed invention is shown, as seen from the perspective of the line 1400 bisecting the device 140 from FIG. 14, and with like numbers representing like features from FIG. 14. The device includes a concave sweat collector 1436 having a determined area of contact with a wearer's skin 12. The sweat collector 1436 is concave in shape, and has sufficient clearance from skin so that when the device is secured to the skin, sweat can freely flow into the device at a natural sweat rate. When applied to a wearer's skin, some of the skin will bulge into the collection area, which aids in providing a seal with skin, but also potentially occludes sweating if the collector is allowed to apply pressure to the sweat ducts. See Johnson, C. E., et al., "The use of partial sweat duct occlusion in the elucidation of sweat duct function in health and disease," *J. Soc. Cosmet. Chem.* 24 15-29 (1973). Some embodiments may include internal ridges to maintain space for sweat to flow to the inlet 1432. The sweat collector also includes a flexible sealing component 1438, which is, for example, a latex or rubber o-ring, a screen-printed silicone gasket, flexible injection-molded ridge, or other suitable material. The sealing component 1438 is configured to prevent sweat entering the collection area from the surrounding skin, and to reduce contamination from the skin surface when the device shifts position during normal wear.

The combination of volumetric sweat rate, sweat conductivity, and GSR in a sweat sensing device as described allows the disclosed method to exploit powerful redundancies and comparative advantages to extend and improve sweat rate and sweat ion concentration estimates. For example, by using contemporaneous GSR, sweat conductivity, and volumetric sweat rate readings as redundant sweat rate estimates, the disclosed method can provide more reliable estimates than one or two of the modalities working alone. Together, these modalities can provide a composite sweat rate estimate, for example, by calculating a weighted average of the three estimates, or by using the estimates to create a profile. Comparisons between volumetric sweat rate, GSR-derived sweat rate, and conductivity-derived sweat rate can therefore be built to provide a calibrated profile for an individual over multiple uses, or for a device over a single use.

Figure 15:
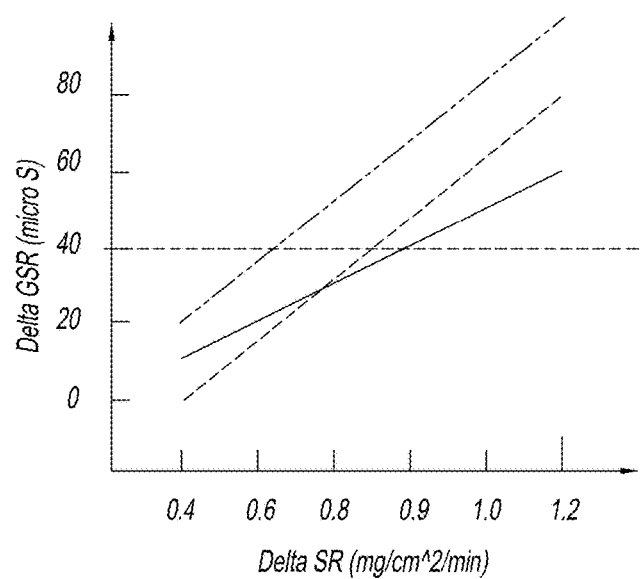
FIG. 15 is a graph depicting ΔGSR to ΔSweat Rate curves for use with the disclosed device and method.

By exploiting comparative advantages among the three modalities, however, the disclosed invention offers benefits in addition to merely providing redundancy. Volumetric sweat rate, by providing a measure of sweat rate that is independent of ionic content, can inform the relative contributions of sweat rate to sweat conductivity and GSR. For example, if GSR changes, contemporaneous volumetric sweat rate can isolate GSR contributions from skin contact resistance changes. While not independent, sweat conductivity also can be compared to GSR to isolate the contribution of skin contact resistance. In this way, volumetric sweat rate measurements can be used to calibrate sweat conductivity and GSR estimates of sweat rate. During the linear phase of sweating, i.e., above 0.4 µL/cm²/min, changes in GSR are proportional to changes in sweat rate. However, absent an independent measure of sweat rate, the ΔGSR to ΔSweat Rate curve cannot be reliably graphed, since both the slope of the curve and its magnitude are unknown. See, e.g., FIG. 15, depicting a 40 μS ΔGSR measurement that corresponds to different sweat rate values, as well as different curve slopes. However, with volumetric sweat rate, the curve's slope and magnitude can be ascertained, and calibrated on a day-to-day, or individual-to-individual basis.

GSR's superior responsiveness to sweat onset and cessation similarly provides useful points of comparison for volumetric sweat rate and sweat conductivity. For example, during periods of decreasing or zero sweat rates, GSR will be the first sensor modality to respond. When the GSR sensor registers an indication of decreasing sweat rate, the device can primarily rely on GSR for sweat rate information, rather than sweat conductivity. GSR can also be used to inform sweat rates during periods that sweat is filling channel sections between switches of the volumetric sensor. For example, as sweat fills between switches in the volumetric sensor, a steady GSR reading confirms that the prospective rate estimate remains accurate. If GSR increases, indicating an increased sweat rate, the device can switch to GSR as the reported prospective sweat rate estimate, and then can retrospectively recalculate the sweat rate when the next switch is reached. GSR provides the most value during decreased sweat rates, which is a particular weakness of the volumetric sensor, since the volumetric sensor is unable to identify the timing or magnitude of a rate decrease. In this scenario, GSR can indicate the timing of the sweat rate decrease, which can then be factored into the retrospective estimates of sweat rate. The calibrated ΔGSR to ΔSweat Rate curve can then allow the device to interpolate between switch contacts in the volumetric sensor, thereby improving sweat rate calculations between switch contacts. Sweat conductivity, while not as responsive as GSR, can similarly inform prospective and retrospective volumetric sweat rate estimates. Used together as described, the three sensor modalities can provide improved calculations of sweat rate and ion concentrations sufficient to detect dehydration, determine fitness level, or characterize the degree of heat acclimation.

In a preferred use, such a capability can inform whether a device wearer has become dehydrated. Studies have indicated that individuals show a significant sweat $Na^+/Cl^-$ spike that can be correlated with dehydration. For example, Gao, et al. (2016) reports an abrupt 10 mM to 30 mM increase in sweat $Na^+$ during the final 10 minutes of a 90-minute dehydration protocol (exercising in hot conditions with no fluid intake; average body weight loss 2.5%). Such a large increase is out of proportion with the change in serum $Na^+/Cl^-$ that is expected from a body weight (fluid) loss of 2.5%, since "precursor sweat" arising in the secretory coil is normally isotonic with interstitial fluid, and 2.5% dehydration would normally increase serum $Na^+/Cl^-$ by only 2-4 mM. See Sato, K., "The physiology, pharmacology, and biochemistry of the eccrine sweat gland," *Rev. Physiol. Biochem. Pharmacol.* 79, 51-131 (1977); James, L. J., et al., "Fluid and electrolyte balance during 24-hour fluid and/or energy restriction," *Int. J. Sport Nutr. Exerc. Metab.* 23, 545-53 (2013); Morgan, R. M., et al., "Acute effects of dehydration on sweat composition in men during prolonged exercise in the heat," *Acta Physiol. Scand.* 182, 37-43 (2004). Not only is the magnitude of the $Na^+/Cl^-$ increase unexpected, but its abruptness indicates the occurrence of something more than a straightforward thermodynamic issue—e.g., hyperosmolality-related sodium reabsorption fighting against a progressively steeper concentration gradient—and points to the role of a regulatory change in the body. Specifically, the 2.5% dehydration threshold is also the point at which thirst typically begins to drive behavioral change, and at which dehydration-related performance decrements become reliably measurable. Therefore, detecting a $Na^+/Cl^-$ concentration spike may indicate the onset of dehydration.

A measure of sweat rate independent of ion content is preferred to identify such a $Na^+/Cl^-$ concentration spike. Since sweat $Na^+$ and $Cl^-$ normally increase with increasing sweat rate, the dehydration spike must be distinguished from expected higher sweat $Na^+/Cl^-$ concentrations that accompany increased sweat rates. With high sweat rate and high $Na^+/Cl^-$ concentration, GSR and sweat conductivity are expected to reflect the changing sweat $Na^+$ and $Cl^-$ levels. Under such circumstances, sweat conductivity will also be higher due to increased lactate production by sweat ducts, which has a disproportionate effect on overall sweat conductivity. An independent sweat rate measure, such as that provided by the volumetric sensor, however, will inform when $Na^+/Cl^-$ increase independently of sweat rate. For example, if the GSR and sweat conductivity sensors detect a $Na^+/Cl^-$ spike while the volumetric sensor indicates a static or decreasing sweat rate, the device can infer that the increased GSR/sweat conductivity readings were cause by increased ionic concentration, rather than sweat rate. Such a spike can then be interpreted as a candidate for a $Na^+/Cl^-$ spike indicative of dehydration. Further, since the rate and magnitude of sweat $Na^+/Cl^-$ increases seen with dehydration greatly exceed increases caused by other conditions, dehydration-related spikes typically need not be distinguished from other causes. The value of the $Na^+/Cl^-$ spike as a predictor of dehydration can be enhanced by incorporating skin temperature measurements. As studies have shown, see, e.g., Morgan, R. M., et al., "Acute effects of dehydration on sweat composition in men during prolonged exercise in the heat," *Acta. Physiol. Scand.* 182, 37-43 (2004); and Collins, K. J., et al., "Observations on arm-bag suppression of sweating and its relationship to thermal sweat-gland 'fatigue'," *J. Physiol.* 161, 538-56 (1962), skin temperature typically begins to rise significantly near the onset of dehydration. Device measurements showing a $Na^+/Cl^-$ spike, combined with dropping sweat rates and increased skin temperature, may therefore be highly indicative of a dehydration state. Another potentially useful measure for predicting dehydration is an increase in heart rate. Therefore, device measurements showing an increase in heart rate, combined with dropping sweat rates and increased skin temperature, would indicate a dehydration state, and the addition of a measured $Na^+/Cl^-$ spike with this combination of readings could add additional certainty to the conclusion.

In addition to providing improved composite sweat rates or sweat rate profiles, GSR and sweat conductivity measurements can also be used to extend informative volumetric sweat rate readings in time. While space limitations allow the disclosed volumetric sensor several hours of operational time under moderately high sweat rates, this amount of operational time, when combined with GSR and sweat conductivity, should allow robust correlation of the device wearer's GSR and sweat conductivity readings to sweat rate. In this way, volumetric sweat rate information obtained early in a device's use cycle can be extrapolated for use after the volumetric sweat rate sensor has filled with sweat or is no longer operational.

While the disclosed method creates an individual, daily, calibration for sweat rate that can support longer-duration measurements, there are potential sources of intra-individual variation that could affect the calibration accuracy within a single measurement period (e.g., one day). These include the hydration status of the device wearer. As discussed above, dehydration can affect both sweat rate and sweat $Na^+/Cl^-$ concentration for a given ΔGSR. Therefore, some embodiments of the disclosed method will account for hydration levels when interpreting ΔGSR to ΔSweat Rate curves. Similarly, local skin temperature variations can affect sweat $Na^+$ concentrations, since $Na^+$ reabsorption relative to sweat rate is reduced at low skin temperature. See Shamsuddin, et al., "Effect of skin temperature on the ion reabsorption capacity of sweat glands during exercise in humans," *Eur. J. Appl. Physiol.* 2005 July:94(4):442-7. This factor may manifest where there is a significant external temperature change during device use, or if the device is subject to significant solar loads. Additionally, during extended duration events, e.g., 6 hours or more, increased cutaneous aldosterone levels can lower sweat $Na^+$ concentrations, since aldosterone acts to increase $Na^+$ reabsorption by the eccrine sweat ducts. See Sato, K., et al., "The effect of intracutaneous d-aldosterone and hydrocortisone on human eccrine sweat gland function," *J. Invest. Dermatol.*, 1970 June:54(6):450-62. Aldosterone increases therefore could be an issue for ultra-endurance athletes, where $Na^+$ concentrations relative to sweat rate may be altered in the latter stages an event, e.g., after 6+ hours.

In other embodiments, the device may include components for stimulating sweat (not shown), such as iontophoresis electrodes, sweat stimulating chemicals (e.g., carbachol, pilocarpine), and other necessary components. In some embodiments, the disclosed invention will be combined with additional sweat sensing device components and capabilities. For example, with further reference to FIG. 14, the channel 1430 may be in fluid communication with a wicking material or chamber that brings the sweat sample to additional sensors, (e.g., ion selective electrode sensors, electrochemical aptamer-based sensors, temperature, pH, enzymatic sensors, immunoassays), sweat sample concentration components, or other components.

This has been a description of the disclosed invention along with a preferred method of practicing the invention, however the invention itself should only be defined by the appended claims.

What is claimed is:

1. A sweat sensing device configured to be worn on an individual's skin, comprising:
   a sweat collector, comprising a concave surface facing the skin, a substantially circular seal, and a fluid port, wherein the concave surface creates a clearance from the skin to promote natural flow of sweat, wherein the seal interacts with the skin to create a coverage area within the collector that is determined, and wherein the seal is configured to substantially prevent sweat from exiting the coverage area from skin located inside the coverage area, and to substantially prevent sweat and surface contaminants from entering the coverage area from skin located outside the coverage area, and wherein the fluid port is in fluidic communication with the microfluidic channel inlet;
   a microfluidic channel for receiving and transporting a sweat sample, wherein the channel has an inlet at a first end, an outlet at a second end, and has a known volume;
   a plurality of GSR electrodes for measuring galvanic skin response ("GSR"), wherein said GSR electrodes are configured to contact the individual's skin when the device is being worn, and wherein the GSR electrodes are located outside the seal of the sweat collector;
   a plurality of conductivity electrodes for measuring sweat conductivity, wherein said conductivity electrodes are in fluid communication with said channel, and wherein the conductivity electrodes are located proximate to the first end of the channel; and
   a volumetric sweat rate sensor, wherein the volumetric sensor includes a detection circuit that includes a plurality of sweat rate electrodes, wherein said sweat rate electrodes intersect said channel at known intervals, where said sweat rate electrodes are in fluid communication with the channel, wherein said sweat rate electrodes divide the channel into a plurality of channel sections, and wherein a plurality of primary sweat rate electrodes located proximate to the channel's first end are separated by a first interval, and a plurality of secondary sweat rate electrodes located proximate to the channel's second end are separated by a second interval, and wherein the second interval is greater than the first interval.

2. The device of claim 1, further including at least one of the following: an electrochemical aptamer-based sensor; a micro-thermal flow rate sensor; and a pressure-based flow rate sensor.

3. The device of claim 1, wherein the microfluidic channel includes at least one of the following to reduce air bubble interference with at least one electrode: an air bubble vent; and an air trap.

4. A wearable sweat sensing device configured to volumetrically determine sweat rate, and configured to be placed on an individual's skin, comprising:
   a sweat collector, comprising a concave surface facing the skin, a substantially circular seal, and a fluid port, wherein the concave surface creates a clearance from the skin to promote natural flow of sweat, wherein the seal interacts with the skin to create a coverage area within the collector that is determined, and wherein the seal is configured to substantially prevent sweat from exiting the coverage area from skin located inside the coverage area, and to substantially prevent sweat and surface contaminants from entering the coverage area from skin located outside the coverage area, and wherein the fluid port is in fluidic communication with the microfluidic channel inlet;
   a microfluidic channel for receiving and transporting a sweat sample, wherein the channel has an inlet at a first end, an outlet at a second end, has a known volume, has a serpentine layout, and at least one surface with a hydrophobic coating; and
   a detection circuit that includes a plurality of electrodes, wherein said electrodes intersect said channel at known intervals, wherein said electrodes are in fluid communication with the channel, and wherein said electrodes divide the channel into a plurality of channel sections, and wherein a plurality of primary electrodes located proximate to the channel's first end are separated by a first interval, a plurality of secondary electrodes located between the primary electrodes and the channel's second end are separated by a second interval, a plurality of tertiary electrodes located between the secondary electrodes and the channel's second end are separated by a third interval, and wherein the third interval is greater than the second interval, and the second interval is greater than the first interval.

5. The device of claim 4, wherein the electrodes are configured as a plurality of interdigitated electrode switches that reroute current upon contact with the sweat sample.

6. The device of claim 4, wherein the channel has one of the following arrangements: constant cross section; and variable cross section.

7. The device of claim 4, further including at least one of the following: a micro-thermal flow rate sensor; a capacitive skin proximity sensor; and an accelerometer.

8. The device of claim 4, wherein said sweat rate is developed using aggregated sweat sensor data that is correlated to relevant external information, wherein the external information includes at least one of the following: air temperature, humidity, the individual's age, the individual's heartrate, the individual's initial hydration state, the individual's fluid intake, the individual's body mass index, the individual's kidney health, the individual's fitness level, and the individual's recent physical activity.

\* \* \* \* \*